(12) United States Patent
Chau et al.

(10) Patent No.: US 10,324,034 B2
(45) Date of Patent: Jun. 18, 2019

(54) SELF-REFERENCING LOCALIZED PLASMON RESONANCE SENSING DEVICE AND SYSTEM THEREOF

(71) Applicant: National Chung Cheng University, Chia-Yi (TW)

(72) Inventors: Lai-Kwan Chau, Chiayi (TW); Chin-Wei Wu, Hsinchu (TW); Chang-Yue Chiang, Taiping (TW); Chien-Hsing Chen, New Taipei (TW)

(73) Assignee: National Chung Cheng University, Chia-Yi (TW)

( * ) Notice: Subject to any disclaimer, the term of this patent is extended or adjusted under 35 U.S.C. 154(b) by 518 days.

(21) Appl. No.: 15/048,828

(22) Filed: Feb. 19, 2016

(65) Prior Publication Data

US 2016/0169797 A1   Jun. 16, 2016

Related U.S. Application Data

(63) Continuation-in-part of application No. 12/806,315, filed on Aug. 10, 2010, now abandoned.

(30) Foreign Application Priority Data

Oct. 20, 2009 (TW) ................. 98135503 A

(51) Int. Cl.
*G01N 21/552* (2014.01)

(52) U.S. Cl.
CPC ..... *G01N 21/554* (2013.01); *G01N 2201/088* (2013.01)

(58) Field of Classification Search
None
See application file for complete search history.

(56) References Cited

U.S. PATENT DOCUMENTS

| 4,879,454 A | 11/1989 | Gerdt |
| 5,494,798 A * | 2/1996 | Gerdt ................. C12Q 1/6825 356/448 |
| 2004/0186359 A1 | 9/2004 | Beaudoin et al. |

OTHER PUBLICATIONS

Chau et al., "Fiber-optic chemical and biochemical probes based on localized surface plasmon resonance," Mar. 9, 2005, Sensors and Actuators B 113 (2006), pp. 100-105.

(Continued)

*Primary Examiner* — Rebecca L Martinez
(74) *Attorney, Agent, or Firm* — Muncy, Geissler, Olds & Lowe, P.C.

(57) ABSTRACT

A self-referencing localized plasmon resonance sensing device and a system thereof are disclosed. The reference optical waveguide element is modified with a noble metal nanoparticle layer. The sensing optical waveguide element is modified with a noble metal nanoparticle layer, which is further modified with a recognition unit. The incident light is guided into the reference and the sensing optical waveguide elements to respectively generate localized plasmon resonance sensor signals. The reference and the sensing optical waveguide elements respectively have a calibration slope. The processor utilizes the calibration slopes to regulate the second difference generated by detecting with the sensing optical waveguide element. The processor utilizes a difference between the first difference, which is generated by detecting with the reference optical waveguide element, and the regulated second difference to obtain a sensor response.

23 Claims, 27 Drawing Sheets

(56) References Cited

OTHER PUBLICATIONS

Peng et al., Novel Dual-channel Fiber-optic Surface Plasmon Resonance Sensors for Biological Monitoring, 2006, Smart Structures and Materials 2006: Smart Sensor Monitoring Systems and Applications, Proc. of SPIE, vol. 6167 61670S.

* cited by examiner

SELF-REFERENCING LOCALIZED PLASMON RESONANCE SENSING DEVICE AND SYSTEM THEREOF

CROSS-REFERENCE TO RELATED APPLICATION

This application is a continuation-in-part of prior U.S. patent application Ser. No. 12/806,315, filed on Aug. 10, 2010, which claims benefit of Taiwan Patent Application No. 098135503, filed on Oct. 20, 2009. The patent application identified above is incorporated here by reference in its entirety to provide continuity of disclosure.

BACKGROUND OF THE INVENTION

1. Field of the Invention

The present invention relates to a localized plasmon resonance sensing device and a system thereof; in particular, it relates to a self-referencing localized plasmon resonance sensing device and a system thereof.

2. Description of the Related Art

The electron cloud on the surface of metal nanoparticles can be excited by an electromagnetic field of a specific frequency, which is resonant with the collective oscillation of the conduction electrons confined within the volume of the nanoparticles, accordingly also known as the Localized Plasmon Resonance (LPR), as shown in FIG. 1. The noble metal nanoparticle 1 generates an intense absorption band in the absorption spectrum, which is referred as the localized plasmon resonance band. The fundamental principle of the localized plasmon resonance sensing system is that, upon conjugation of a recognition unit on the surface of noble metal nanoparticle 1 and a target binds with the recognition unit, the target accordingly covers the vicinity of the surface on the noble metal nanoparticle 1, such that a change occurs in the surrounding dielectric environment at which the noble metal nanoparticle 1 is located and whose peak wavelength position and absorption are extremely sensitive to variation in the dielectric constant of the exterior surrounding, thus leading to alternation in the LPR resonance band; and finally by means of modifying the recognition unit for enabling specific detection capability, then through analysis on the relationship between the variation in the frequency or absorption of the resonance band and the concentration of the target, it is possible to establish a quantitative detection method. The method basically comprises modifying the noble metal nanoparticles on an optical waveguide, thereby forming a noble metal nanoparticle layer thereon. The said noble metal nanoparticle layer is made by one of the sphere-shaped noble metal nanoparticle, the cube-shaped noble metal nanoparticle, the prism-shaped noble metal nanoparticle, the rod-shaped noble metal nanoparticle and the shell-shaped noble metal nanoparticle, with essentially no connections existing between the nanoparticles, and the noble metal may be gold, silver or platinum. By using the effect of multiple total internal reflections along an optical waveguide, it is possible to accumulate the amount of change in the absorption of the evanescent wave due to absorption by the nanoparticle plasmon resonance so as to enhance the LPR signal for sensing operations. Meanwhile, through modification of the surface of the noble metal nanoparticle 1 with various recognition units, the functionalized noble metal nanoparticles can be applied to detection of various targets.

The single fiber-optic LPR sensing system lacks the ability to compensate influences caused by instrumental or environmental factors, such as baseline drift due to instability of the light source, and changes in the temperature or the composition of the solution to be tested, since the LPR sensing technology employs the sensitivity of the noble metal nanoparticle to the refractive index in the surrounding environment as a way to detect biological molecules, which is also dependent on the temperature or the composition of the samples. During detection of real samples, it is commonly required to control the temperature of the sample or undergo dilution more than two times in the sample preparation processes. An addition of temperature control system may increase system complexity while multiple dilutions may undesirably degrade the effective detection limit.

SUMMARY OF THE INVENTION

Regarding to the aforementioned drawbacks in prior art, the objective of the present invention is to provide a self-referencing localized plasmon resonance sensing device and a system thereof in order to eliminate the interferences induced by environmental factors or dielectric properties inherent in the sample itself, and also resolve the issue of nonspecific adsorption.

According to an objective of the present invention, a self-referencing localized plasmon resonance sensing device is herein provided. The self-referencing localized plasmon resonance sensing device comprises a reference optical waveguide element, a sensing optical waveguide element, and a carrier. The optical waveguide element can be an optical fiber, a channel waveguide, a planar waveguide, or a tubular waveguide, and so on. Preferably, the optical waveguide element is an optical fiber. The reference optical waveguide element is modified with a first noble metal nanoparticle. Part of an incident light is guided into the reference optical waveguide element, wherein the light is under total internal reflections many times along the reference optical waveguide element, to generate a first localized plasmon resonance sensor signal. The first localized plasmon resonance sensor signal includes a first signal generated by detecting a blank with the reference optical waveguide element and a second signal generated by detecting a sample with the reference optical waveguide element. The reference optical waveguide element has a first calibration slope. Besides, the sensing optical waveguide element is modified with a second noble metal nanoparticle layer. The second noble metal nanoparticle layer is further modified with a recognition unit. The other part of the incident light is guided into the sensing optical waveguide element, wherein the light is under total internal reflections many times along the sensing optical waveguide element, to generate a second localized plasmon resonance sensor signal. The second localized plasmon resonance sensor signal includes a third signal generated by detecting the blank with the sensing optical waveguide element and a fourth signal generated by detecting the sample with the sensing optical waveguide element. The sensing optical waveguide element has a second calibration slope. Here, a processor normalizes a first difference between the second signal and the first signal and normalizes a second difference between the fourth signal and the third signal. The processor utilizes the first calibration slope and the second calibration slope to regulate the second difference, which is normalized, for obtaining a regulated second difference. Then, the processor utilizes a difference between the first difference, which is normalized, and the regulated second difference to obtain a sensor response. Besides, the carrier places the reference optical waveguide element and the sensing optical waveguide element.

Preferably, the first noble metal nanoparticle layer is modified at a reflecting surface of the reference optical waveguide element.

Preferably, the second noble metal nanoparticle layer is modified at a reflecting surface of the sensing optical waveguide element.

Preferably, when the reference optical waveguide element is an optical fiber, the first noble metal nanoparticle layer can be modified at a stripped area or an end face of the optical fiber.

Preferably, when the sensing optical waveguide element is an optical fiber, the second noble metal nanoparticle layer can be modified at a stripped area or an end face of the optical fiber.

Preferably, the reference optical waveguide element and the sensing optical waveguide element are optical fibers, channel waveguides, planar waveguides, or tubular waveguides.

Preferably, the self-referencing optic localized plasmon resonance sensing device is a microfluidic chip or an in-situ sampling and analysis device.

Preferably, the reference optical waveguide element and the sensing optical waveguide element are respectively constructed with a mirror at one end face of the reference optical waveguide element and at one end face of the sensing optical waveguide element, wherein the reference optical waveguide element and the sensing optical waveguide element are optical fibers or tubular waveguides.

Preferably, the reference optical waveguide element and the sensing optical waveguide element are further disposed with a filter membrane and a rigid holder with at least one opening. The mirrors are provided for reflecting the first localized plasmon resonance sensor signal and the second localized plasmon resonance sensor signal, the filter membrane sieves out interfering substances with sizes larger than that of the average pore size of the membrane. Besides, the rigid holder encases the reference optical waveguide element and the sensing optical waveguide element in order to enhance the mechanical strength of the device during the sampling operation.

Preferably, the recognition unit comprises a chemical recognition molecule, an antibody, an antigen, a lectin, a hormone receptor, a nucleic acid or a carbohydrate.

Preferably, the sensor response are expressed by the following equation:

$$\frac{\Delta I_{S,SA}}{I_{S0}} = \frac{\Delta I_S}{I_{S0}} - \frac{\Delta I_{S,M}/I_{S0}}{\Delta I_{R,M}/I_{R0}} \times \frac{\Delta I_R}{I_{R0}};$$

wherein $\Delta I_{S,SA}$ represents the sensor response due to specific adsorption only, $I_{S0}$ represents the third signal generated by detecting the blank with the sensing optical waveguide element, $\Delta I_S$ represents the second difference between the fourth signal and the third signal, $\Delta I_{S,M}/I_{S0}$ and $\Delta I_{R,M}/I_{R0}$ respectively represent a normalized response of the sensing optical waveguide element and the reference optical waveguide element, which respectively indicate the second calibration slope and the first calibration slope, $\Delta I_R$ represents the first difference between the second signal and the first signal, and $I_{R0}$ represents the first signal generated by detecting the blank with the reference optical waveguide element.

According to another objective of the present invention, a self-referencing localized plasmon resonance sensing system is herein provided. The self-referencing localized plasmon resonance sensing system comprises a light source, a localized plasmon resonance sensing device, at least one photodiode, and a processor. The light source generates an incident light. The localized plasmon resonance sensing device comprises a reference optical waveguide element, a sensing optical waveguide element, and a carrier. Here, the reference optical waveguide element is modified with a first noble metal nanoparticle layer. Part of an incident light is guided into the reference optical waveguide element to generate a first localized plasmon resonance sensor signal. The reference optical waveguide element has a first calibration slope. Besides, the sensing optical waveguide element is modified with a second noble metal nanoparticle layer. The second noble metal nanoparticle layer is further modified with a recognition unit. The other part of the incident light is guided into the sensing optical waveguide element to generate a second localized plasmon resonance sensor signal. The sensing optical waveguide element has a second calibration slope. Besides, the carrier places the reference optical waveguide element and the sensing optical waveguide element. Besides, the at least one photodiode receives the first localized plasmon resonance sensor signal and the second localized plasmon resonance sensor signal. Here, the first localized plasmon resonance sensor signal includes a first signal generated by detecting a blank with the reference optical waveguide element and a second signal generated by detecting a sample with the reference optical waveguide element. The second localized plasmon resonance sensor signal includes a third signal generated by detecting the blank with the sensing optical waveguide element and a fourth signal generated by detecting the sample with the sensing optical waveguide element. Besides, the processor normalizes a first difference between the second signal and the first signal and normalizes a second difference between the fourth signal and the third signal. Here, the processor utilizes the first calibration slope and the second calibration slope to regulate the second difference, which is normalized, for obtaining a regulated second difference. Then, the processor utilizes a difference between the first difference, which is normalized, and the regulated second difference to obtain a sensor response.

Preferably, the first noble metal nanoparticle layer is modified at a reflecting surface of the reference optical waveguide element.

Preferably, the second noble metal nanoparticle layer is modified at a reflecting surface of the sensing optical waveguide element.

Preferably, when the reference optical waveguide element is an optical fiber, the first noble metal nanoparticle layer can be modified at a stripped area or an end face of the optical fiber.

Preferably, when the sensing optical waveguide element is an optical fiber, the second noble metal nanoparticle layer can be modified at a stripped area or an end face of the optical fiber.

Preferably, the reference optical waveguide element and the sensing optical waveguide element are optical fibers, channel waveguides, planar waveguides, or tubular waveguides.

Preferably, the self-referencing localized plasmon resonance sensing device is a microfluidic chip or an in-situ sampling and analysis device.

Preferably, the reference optical waveguide element and the sensing optical waveguide element are respectively constructed with a mirror at one end face of the reference optical waveguide element and at one end face of the sensing optical waveguide element, wherein the reference optical waveguide element and the sensing optical waveguide element are optical fibers or tubular waveguides.

Preferably, the reference optical waveguide element and the sensing optical waveguide element are further disposed with a filter membrane and a rigid holder with at least one opening. The mirrors are provided for reflecting the first localized plasmon resonance sensor signal and the second localized plasmon resonance sensor signal. The filter membrane sieves out interfering substances with sizes larger than that of the average pore size of the membrane. The rigid holder encases the reference optical waveguide element and the sensing optical waveguide element in order to enhance the mechanical strength of the device during the sampling operation.

Preferably, the recognition unit comprises a chemical recognition molecule, an antibody, an antigen, a lectin, a hormone receptor, a nucleic acid or a carbohydrate.

Preferably, the self-referencing localized plasmon resonance sensing system of the present invention further comprises a lock-in amplifier enabling amplification of the first localized plasmon resonance sensor signal and the second localized plasmon resonance sensor signal as well as suppression of system noises.

Preferably, the sensor response are expressed by the following equation:

$$\frac{\Delta I_{S,SA}}{I_{S0}} = \frac{\Delta I_S}{I_{S0}} - \frac{\Delta I_{S,M}/I_{S0}}{\Delta I_{R,M}/I_{R0}} \times \frac{\Delta I_R}{I_{R0}};$$

wherein $\Delta I_{S,SA}$ represents the sensor response due to specific adsorption only, $I_{S0}$ represents the third signal generated by detecting the blank with the sensing optical waveguide element, $\Delta I_S$ represents the second difference between the fourth signal and the third signal, $\Delta I_{S,M}/I_{S0}$ and $\Delta I_{R,M}/I_{R0}$ respectively represent a normalized response of the sensing optical waveguide element and the reference optical waveguide element, which respectively indicate the second calibration slope and the first calibration slope, $\Delta I_R$ represents the first difference between the second signal and the first signal, and $I_{R0}$ represents the first signal generated by detecting the blank with the reference optical waveguide element.

In summary of the descriptions set forth hereinbefore, the self-referencing localized plasmon resonance sensing device and the system thereof according to the present invention allow one or more of the following advantages:

(1) the disclosed self-referencing localized plasmon resonance sensing device and the system thereof are able to reduce interferences caused by environmental factors or dielectric properties inherent in the sample itself, and also resolve the issue of nonspecific adsorption, allowing the sensing system to provide the self-referencing feature thereby improving the detection performance of the self-referencing localized plasmon resonance sensing device and a system thereof on real samples; and (2) the disclosed self-referencing localized plasmon resonance sensing device and the system thereof allow, during detection of targets, to lessen the number of dilutions for the samples in the sample preparation processes, thereby improving the detection limit for sensing operations.

DETAILED DESCRIPTION OF THE PREFERRED EMBODIMENTS

Figure 1:
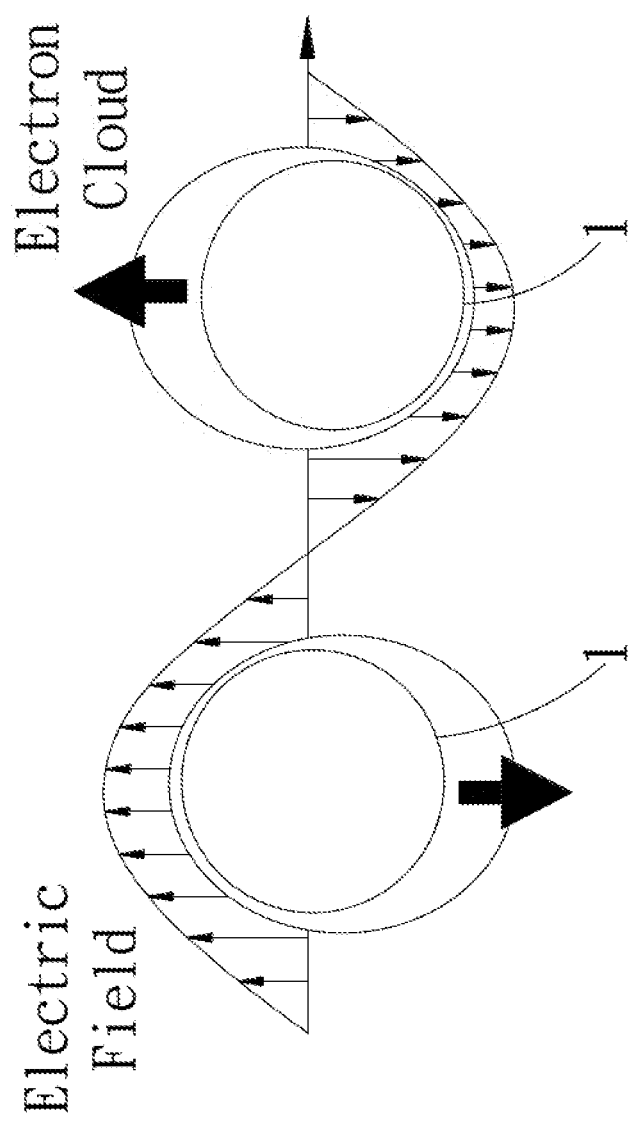
FIG. 1 is a diagram for the localized plasmon resonance in prior art.
Figure 2:
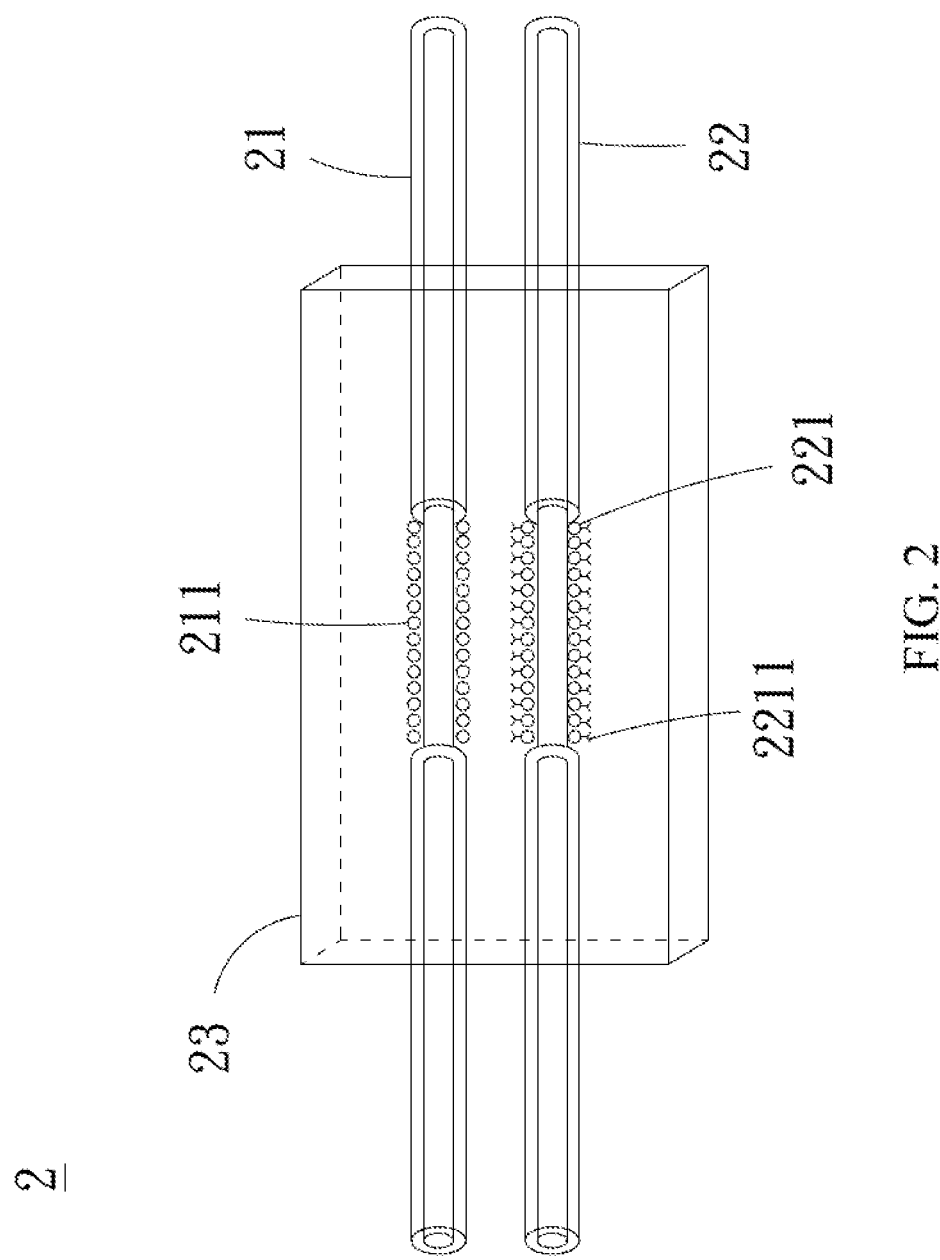
FIG. 2 is a diagram for a self-referencing fiber-optic localized plasmon resonance sensing device according to the present invention.

Refer now to FIG. 2, wherein a diagram for a self-referencing fiber-optic localized plasmon resonance sensing device according to the present invention is shown. In the FIG. 2, the self-referencing fiber-optic localized plasmon resonance sensing device 2 comprises a reference optical fiber 21, a sensing optical fiber 22 and a carrier 23. The reference optical fiber 21 is modified with a first noble metal nanoparticle layer 211 and receives an incident light to generate a first localized plasmon resonance sensor signal. The sensing optical fiber 22 is modified with a second noble metal nanoparticle layer 221. The second noble metal nanoparticle layer 221 is further modified with a recognition unit 2211, and receives the incident light to generate a second localized plasmon resonance sensor signal. The carrier 23 is used for placement of the reference optical fiber 21 and the sensing optical fiber 22, wherein a processing unit is allowed to perform referencing on the second localized plasmon resonance sensor signal based on the first localized plasmon resonance sensor signal. The recognition unit may be a chemical recognition molecule, an antibody, an antigen, a lectin, a hormone receptor, a nucleic acid or a carbohydrate.

Figure 3A:
FIG. 3a is a diagram for an optical fiber according to the present invention whose cladding layer at a certain region of the fiber is stripped entirely.
Figure 3B:
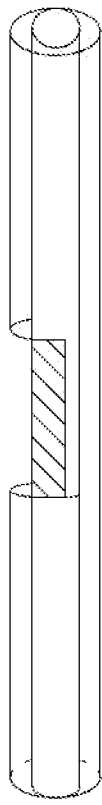
FIG. 3b is a diagram for an optical fiber according to the present invention whose cladding layer at a certain region of the fiber is partially stripped.
Figure 3C:
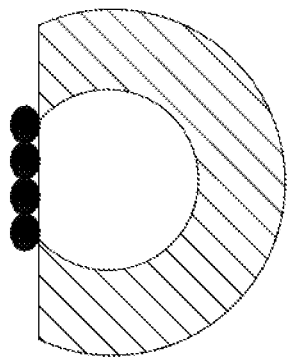
FIGS. 3c and 3d are cross-sectional views for an optical fiber according to the present invention whose cladding layer at a certain region of the fiber is partially stripped.
Figure 3D:
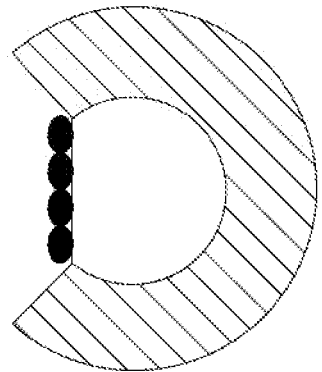
Figure 3E:
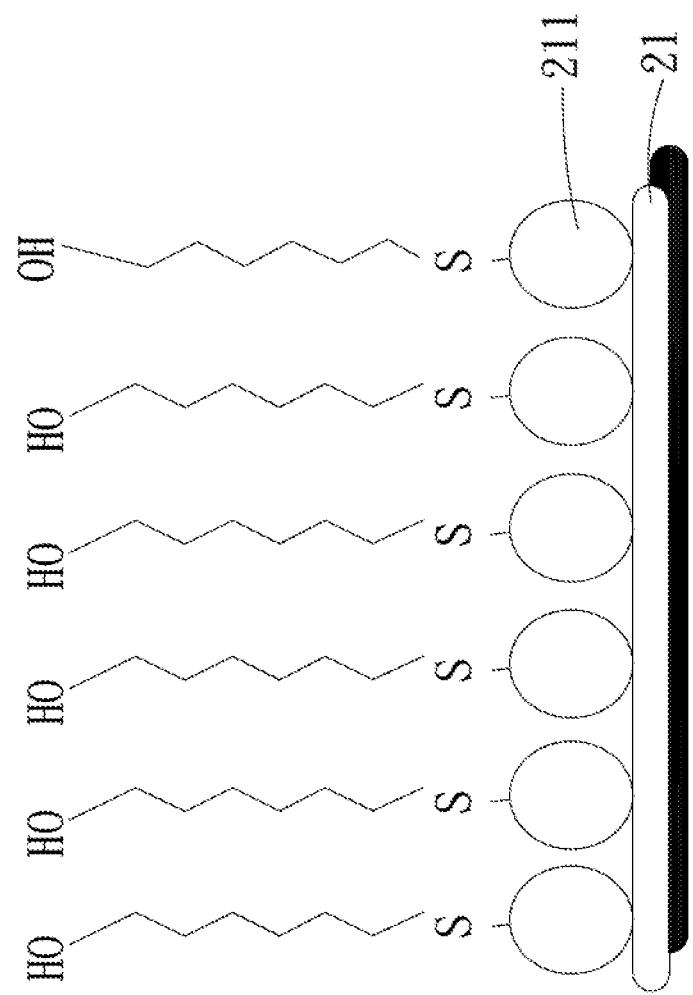
FIG. 3e is a diagram for a reference optical fiber according to the present invention whose noble metal nanoparticle surface is modified with a monolayer having a thiol head group and a hydroxyl end group.

In terms of the reference optical fiber 21 or the sensing optical fiber 22, it is possible to select a region of the optical fiber with the cladding layer thereof entirely stripped, as shown in FIG. 3a, or alternatively a region of the optical fiber with the cladding layer thereof partially stripped, as shown in FIG. 3b. The cross-sectional views for the optical fiber with the cladding layer of a selected region thereof partially stripped are shown in FIGS. 3c and 3d. After removal of the cladding layer, the reference optical fiber 21 can be modified with a first noble metal nanoparticle layer 211 and allowed to be further modified with molecules having a hydroxyl end group (—OH) on the surface of the noble metal nanoparticles so as to provide the surface of the first noble metal nanoparticle layer 211 with hydrophility thereby reducing nonspecific surface adsorption, as shown in FIG. 3e. In order to functionalize molecules with a hydroxyl end group onto the surface of the noble metal nanoparticles, a mercaptohexanol (MCH) solution can be prepared and the reference optical fiber 21 that has the first noble metal nanoparticle layer 211 can be immersed in such the MCH solution for reaction.

Figure 3F:
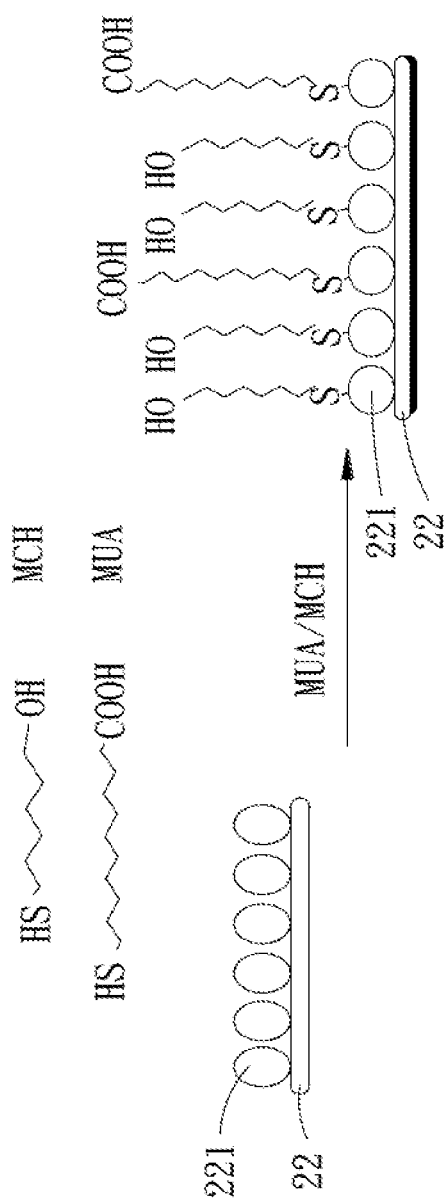
FIG. 3f is a diagram for a sensing optical fiber according to the present invention whose noble metal nanoparticle surface is modified with a mixed monolayer having a thiol head group and a hydroxyl or a carboxylic acid end group.
Figure 3G:
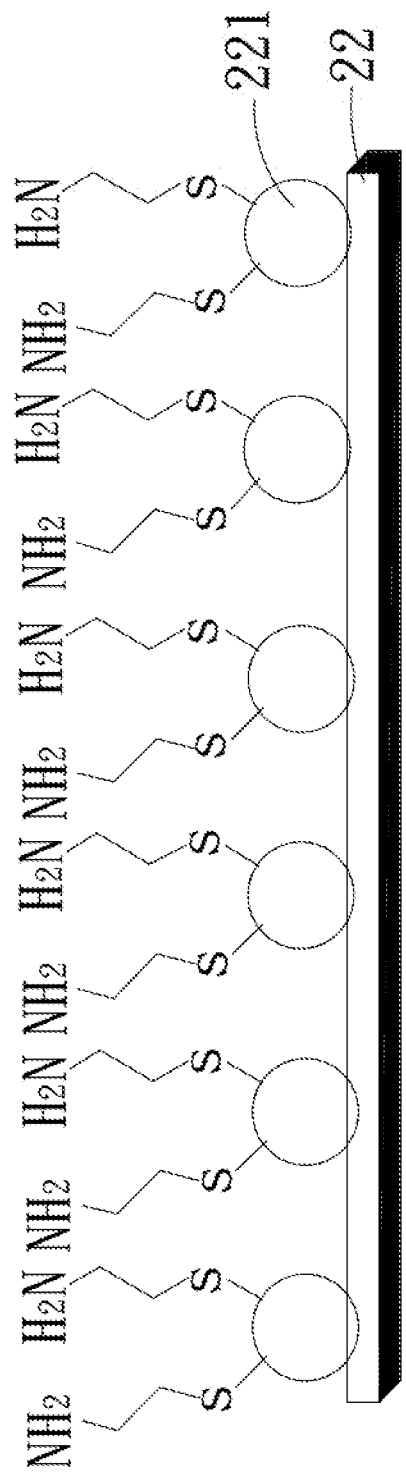
FIG. 3g is a diagram for a sensing optical fiber-optic according to the present invention whose noble metal nanoparticle surface is modified with a monolayer having a thiol head group and an amino end group.

After removal of the cladding layer, the sensing optical fiber 22 is also modified with the second noble metal nanoparticle layer 221 and further modified with a specific recognition unit 2211 on the surface of the noble metal nanoparticle, allowing the sensing optical fiber 22 to have a specific detection capability; for example, the surface of the noble metal nanoparticles may be functionalized with long-chain mercaptan molecules containing a carboxylic acid end group (—COOH) or an amino end group (—NH). In order to have the surface of the noble metal nanoparticle to be functionalized with long-chain mercaptan molecules containing a carboxylic acid end group (—COOH) and reduce the nonspecific surface adsorption, a solution consisting of both 11-mercaptoundecanoic acid (MUA) and mercaptohexanol (MCH) at a 1:4 volume ratio can be used for the self-assembly reaction, as shown in FIG. 3f. By adding in short carbon chain MCH molecules at a particular ratio, it is possible to spatially disperse the distance between individual probe molecule, resolving steric hindrance in antibody-antigen recognition thereby improving recognition efficiency thereof. Alternatively, in order to have the surface of the noble metal nanoparticles to be functionalized with mercaptan molecules containing an amino end group as shown in FIG. 3g, it can be performed to prepare a cystamine solution and immerse the sensing optical fiber 22 which has been modified with the second noble metal nanoparticle layer 221 therein for reaction.

Figure 4A:
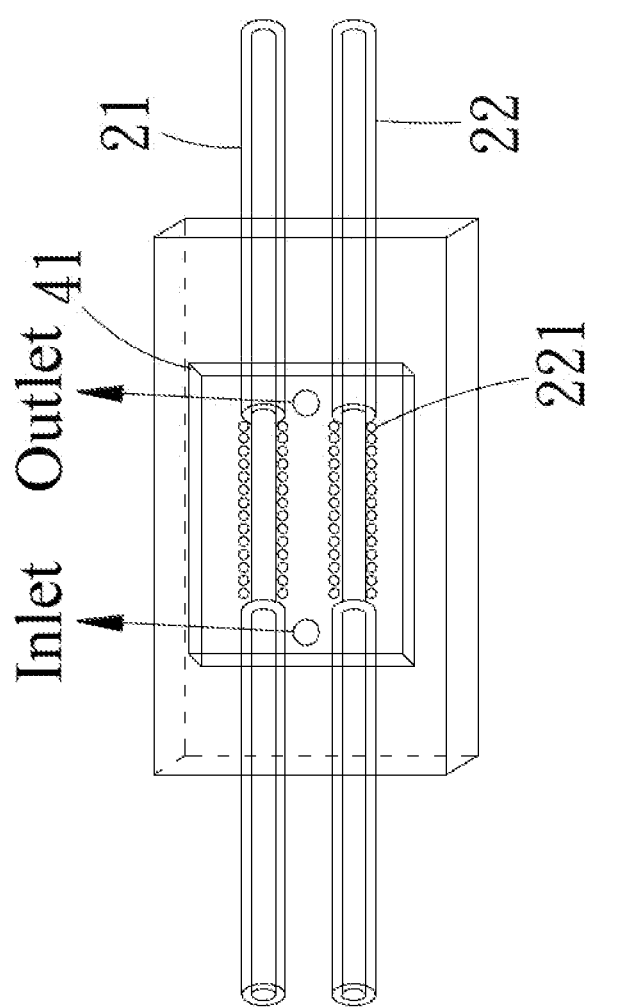
FIG. 4a is a diagram for a first embodiment of the self-referencing fiber-optic localized plasmon resonance sensing device according to the present invention.
Figure 4B:
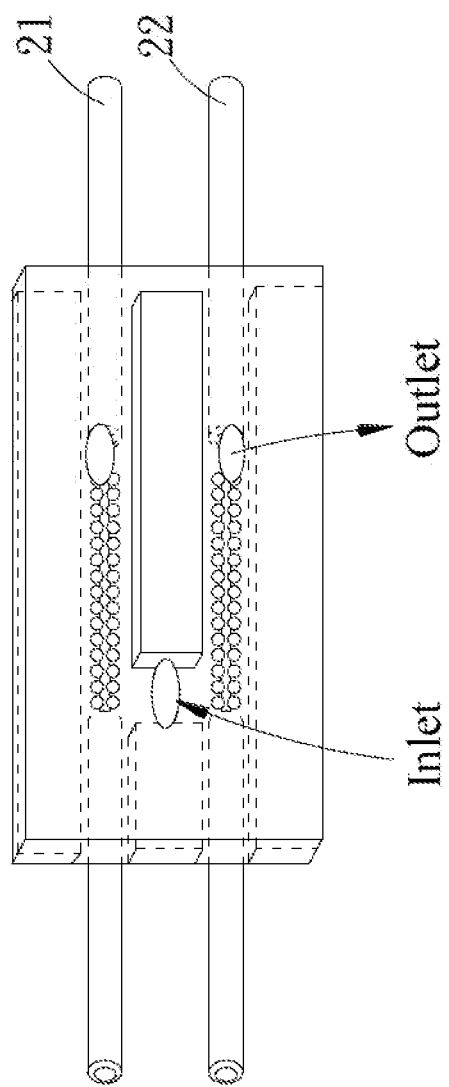
FIG. 4b is a diagram for a second embodiment of the self-referencing fiber-optic localized plasmon resonance sensing device according to the present invention.
Figure 4C:
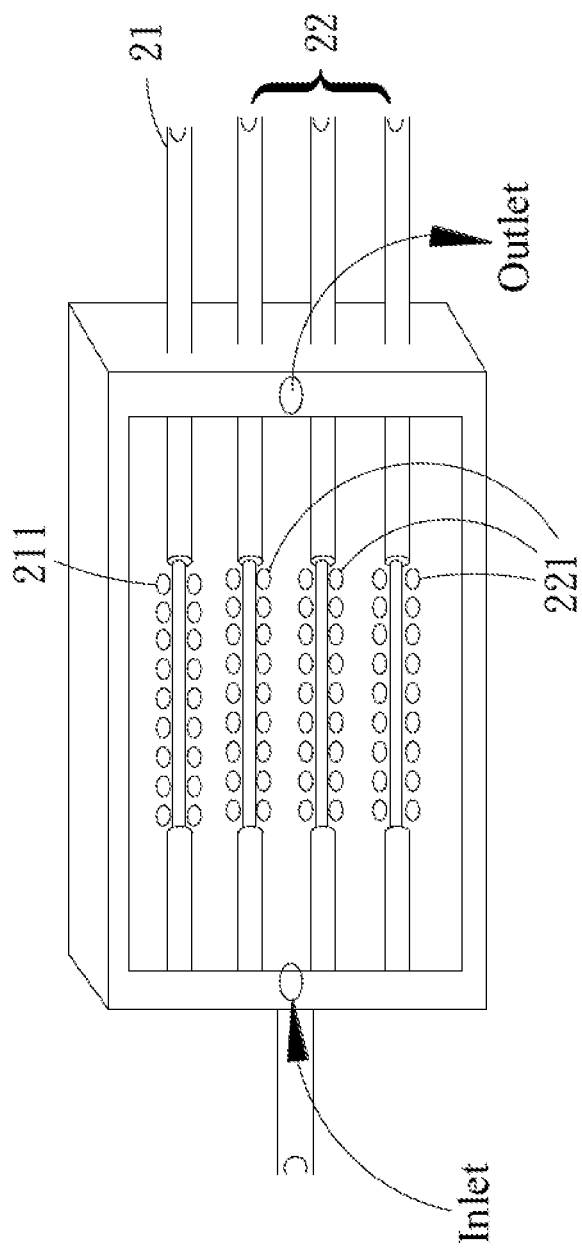
FIG. 4c is a diagram for a third embodiment of the self-referencing fiber-optic localized plasmon resonance sensing device according to the present invention.

Refer now to FIG. 4, wherein a diagram for a first embodiment of the self-referencing fiber-optic localized plasmon resonance sensing device according to the present invention is shown. In case the fiber-optic localized plasmon resonance device 2 is a microfluidic chip, the channel portion thereof can be designed as demand in accordance with the target, in which factors needed to be considered may include fluid dynamics upon introduction of the sample, surface tension, fluid volume, internal pressure and residue of sample after analysis. Furthermore, both internal and external factors during chip packaging may be also essential for considerations. Referring to FIG. 4a, wherein a diagram illustrating a basic microfluidic chip is shown. In this microfluidic chip, a single sample reservoir 41 is appropriately designed for placement of the reference optical fiber 21, the sensing optical fiber 22 and the sample whose volume may be roughly smaller than or equal to 50 microliters. Refer next to FIG. 4b, wherein a diagram for an alternative microfluidic chip according to the present invention is shown. In the FIGs., the sample flows to two microfluidic channels and its volume is approximately smaller than or equal to 40 microliters. Refer also to FIG. 4c, wherein a diagram for a microfluidic chip for multiplex detection is shown, wherein it is allowed to place simultaneously a reference optical fiber 21 and plural sensing optical fibers 22 having different recognition units for multiplex sensing operations. The sample volume required for testing is approximately 20-80 microliters, thereby meeting the requirement of microanalysis for reducing sample consumption and further providing the capability of simultaneous detection of multiple targets for the purpose of time-saving.

Figure 5:
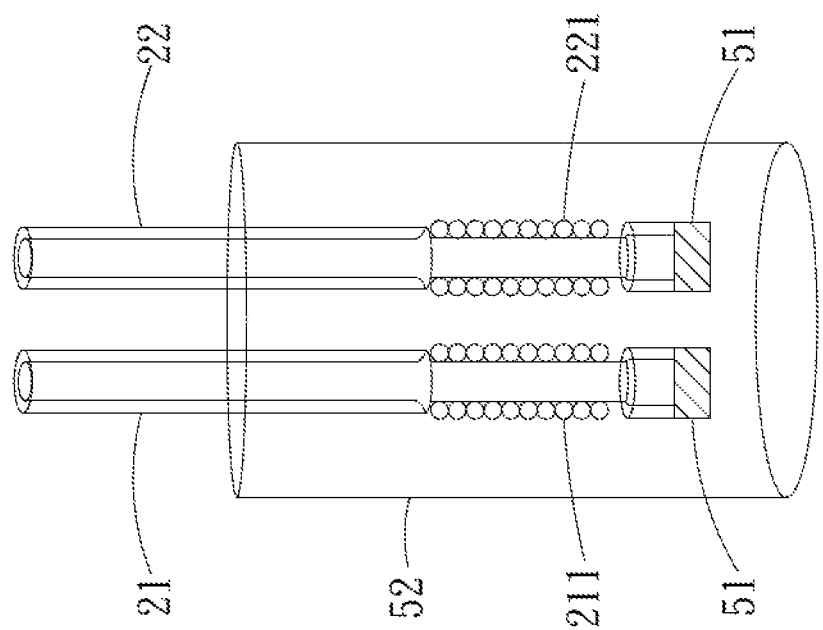
FIG. 5 is a diagram for a second embodiment of the self-referencing fiber-optic localized plasmon resonance sensing device according to the present invention.

Refer subsequently to FIG. 5, wherein a diagram for a second embodiment of the self-referencing fiber-optic localized plasmon resonance device according to the present invention is shown. In case the fiber-optic localized plasmon resonance device 2 is used in a micro sample tray, the reference optical fiber and the sensing optical fiber may be constructed with a mirror 51 at the distal end face of the optical fiber so as to reflect the first localized plasmon resonance sensor signal and the second localized plasmon resonance sensor signal. A filter membrane 52 may be further installed for blocking interfering substances with sizes larger than that of the average pore size of the membrane out of the filter membrane 52.

Figure 6A:
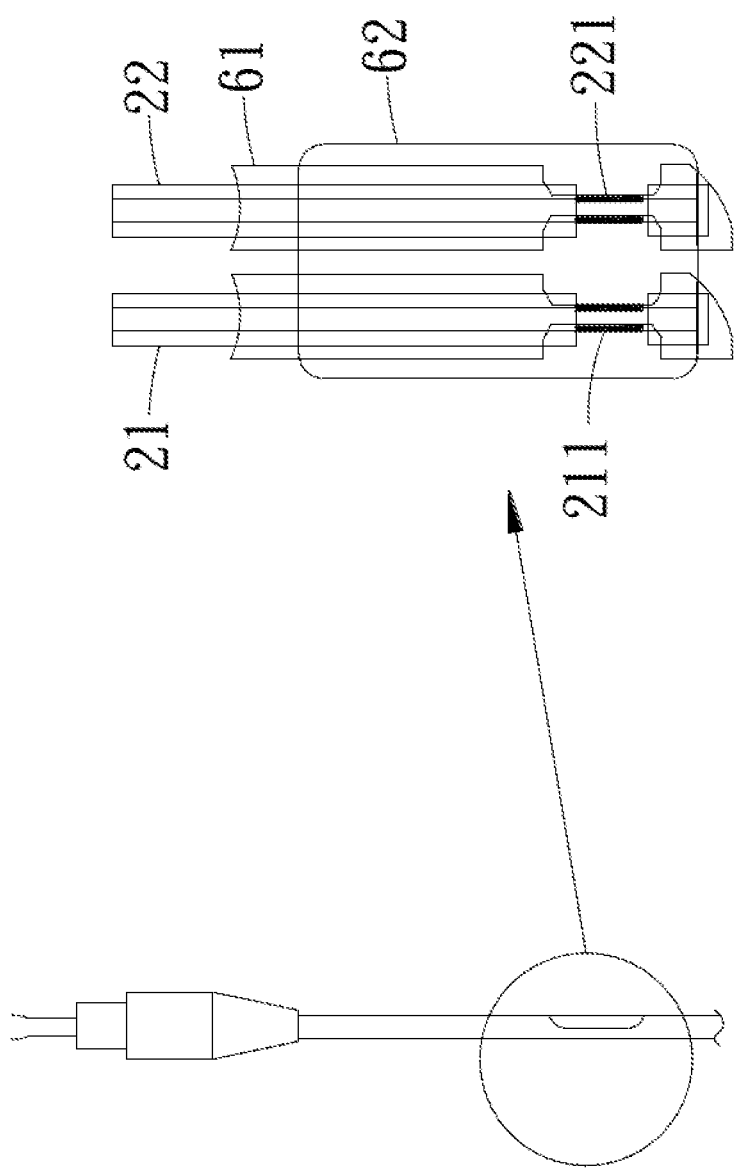
FIG. 6a is a diagram for a third embodiment of the self-referencing fiber-optic localized plasmon resonance sensing device according to the present invention.
Figure 6B:
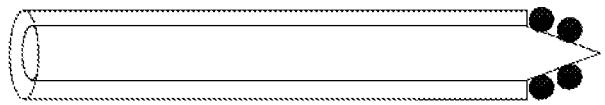
FIG. 6b is a diagram for a reference optical fiber and a sensing optical fiber according to the present invention whose end face is respectively modified with a noble metal nanoparticle layer.
Figure 6B:
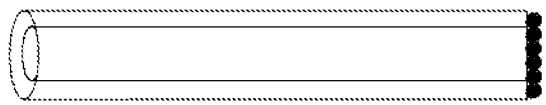

Refer next to FIG. 6a, wherein a diagram for a third embodiment of the self-referencing fiber-optic localized plasmon resonance sensing device according to the present invention is shown. During detection of a real environmental or biological sample or specimen, it is possible to accomplish the in-situ detection by immersion or piercing of the sampling device into a specific sample or object. As a result, the sensing device is suitable for use as an apparatus for medical in-vivo examination or on-site sampling and analysis. During detection of a real sample, there may be various interfering substances existing in the sample, so it is possible to add a filter membrane 62 onto the exterior of the reference optical fiber 21 and the sensing optical fiber 22 so as to isolate interfering substances with sizes larger than that of the average pore size of the membrane out of such filter membrane 62; besides, a rigid holder 61 with a hole configured on the holder thereof may be placed to enhance the physical strength of the entire sensor. Furthermore, it is also possible to modify a noble metal nanoparticle layer 211, 221 respectively on the end face of the reference optical fiber 21 and the sensing optical fiber 22 to facilitate in-situ sampling and analysis, as shown in FIG. 6b.

Figure 7:
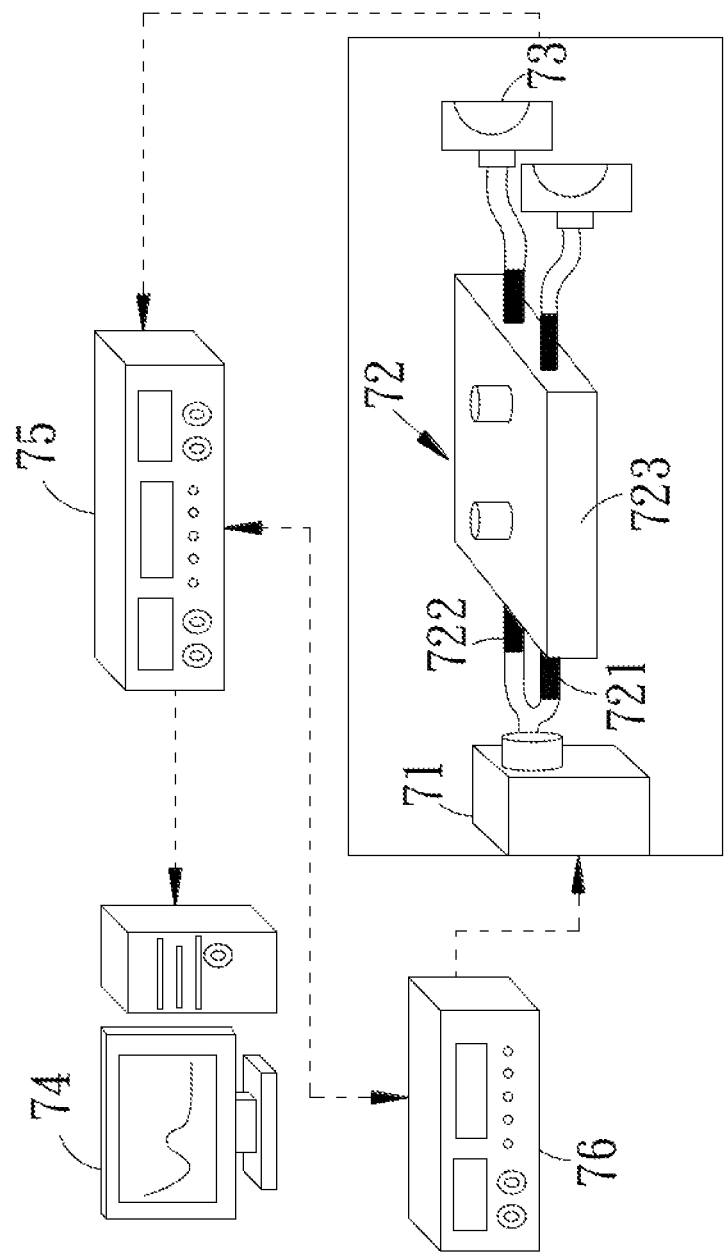
FIG. 7 is a diagram for a self-referencing fiber-optic localized plasmon resonance sensing system according to the present invention.

Refer now to FIG. 7, wherein a diagram for a self-referencing fiber-optic localized plasmon resonance sensing system according to the present invention is shown. The illustrated self-referencing fiber-optic localized plasmon resonance sensing system comprises: a light source 71, a fiber-optic localized plasmon resonance sensing device 72 and a photo detecting unit 73. The light source 71 may be a Light Emitting Diode (LED) for generation of the incident light, wherein the incident light is coupled into the fiber-optic localized plasma resonance sensing device 72 via a fiber-optic coupler. The fiber-optic localized plasmon resonance sensing device 72 comprises a reference optical fiber 721, a sensing optical fiber 722 and a carrier 723. The reference optical fiber 721 is modified with a first noble metal nanoparticle layer, and receives the incident light to generate a first localized plasmon resonance sensor signal. The sensing optical fiber 722 is modified with a second noble metal nanoparticle layer, wherein the second noble metal nanoparticle layer is further modified with a recognition unit, and receives the incident light to generate a second localized plasmon resonance sensor signal. The carrier 723 is used for placement of the reference optical fiber 721 and the sensing optical fiber 722. The photo detecting unit 73 may be a photodiode for receiving the first localized plasmon resonance sensor signal and the second localized plasmon resonance sensor signal. A processing unit 74 is allowed to perform referencing on the second localized plasmon resonance sensor signal based on the first localized plasmon resonance sensor signal. The fiber-optic localized plasmon resonance sensing system further comprises a lock-in amplifier 75 and a signal generator 76, in which the lock-in amplifier 75 enables amplification of the first localized plasmon resonance sensor signal and the second localized plasmon resonance sensor signal as well as suppression of system noises, and the signal generator 76 drives the light source to generate and regulate the incident light, and also provides the lock-in amplifier with a reference signal.

During detection of biological or chemical samples, it is possible to employ the selectivity of the recognition unit for sensing operations at various concentrations, in which the sensing optical fiber 722 is modified with a recognition unit, while the reference optical fiber 721 is not. The dielectric environment within the vicinity of the sensing optical fiber 722 varies as the recognition unit on the surface of the noble metal nanoparticles and the target interacts, thereby decreasing the second localized plasmon resonance sensor signal and the generated temporal signal presents a molecular binding kinetic curve. Since the surface of the reference optical fiber 721 is not modified with the recognition unit, the variations in the first localized plasmon resonance sensor signal simply result from changes in the refraction index of the sample, nonspecific absorptions or other environmental factors. The first localized plasmon resonance sensor signal can be the signal $I_{R0}$, which is obtained upon detecting a blank and the nanoparticle surface of the reference optical fiber 721 not modified with a recognition unit, and the signal $I_R$, which is obtained upon detecting a sample of different concentrations of a target by means the reference optical fiber 721; the second localized plasmon resonance sensor signal can be the signal $I_{S0}$, which is obtained upon detecting the blank and the nanoparticle surface of the sensing optical fiber 722 modified with the recognition unit, and the signal $I_S$, which is obtained upon detecting the sample by means the sensing optical fiber 722. Please refer to the following equations:

$$I'_0 = I_{S0}/I_{R0}$$

$$I' = I_S/I_R$$

$$T' = I'/I'_0 = (I_S/I_R)/(I_{S0}/I_{R0}) = (I_S/I_{S0})/(I_R/I_{R0}) = T_S/T_R$$

The parameters used in the aforementioned equations are respectively illustrated as below: $I'_0$ indicates the corrected signal obtained by the division of the above-said $I_{S0}$ by $I_{R0}$ when detecting the same blank; $I'$ is the corrected signal obtained by the division of the above-said $I_S$ by $I_R$ when detecting the same sample; and $T' = I'/I'_0$ represents the relative signal obtained after self-referencing. After taking the –log value on the concentration of the target as the x-axis, then plotting with respect to $T' = I'/I'_0$ as the y-axis, the linear part of the plot between the relative signal and the –log concentration can be used as a calibration graph.

Figure 8A:
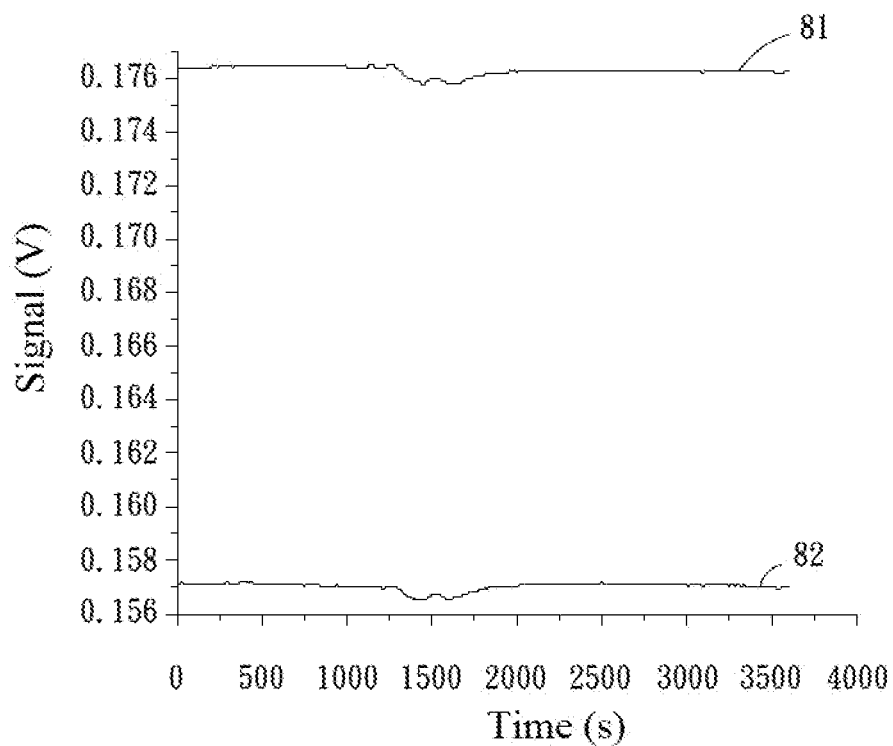
FIG. 8a is a diagram for the signal-time relationships obtained by a first embodiment of the self-referencing fiber-optic localized plasmon resonance system according to the present invention.
Figure 8B:
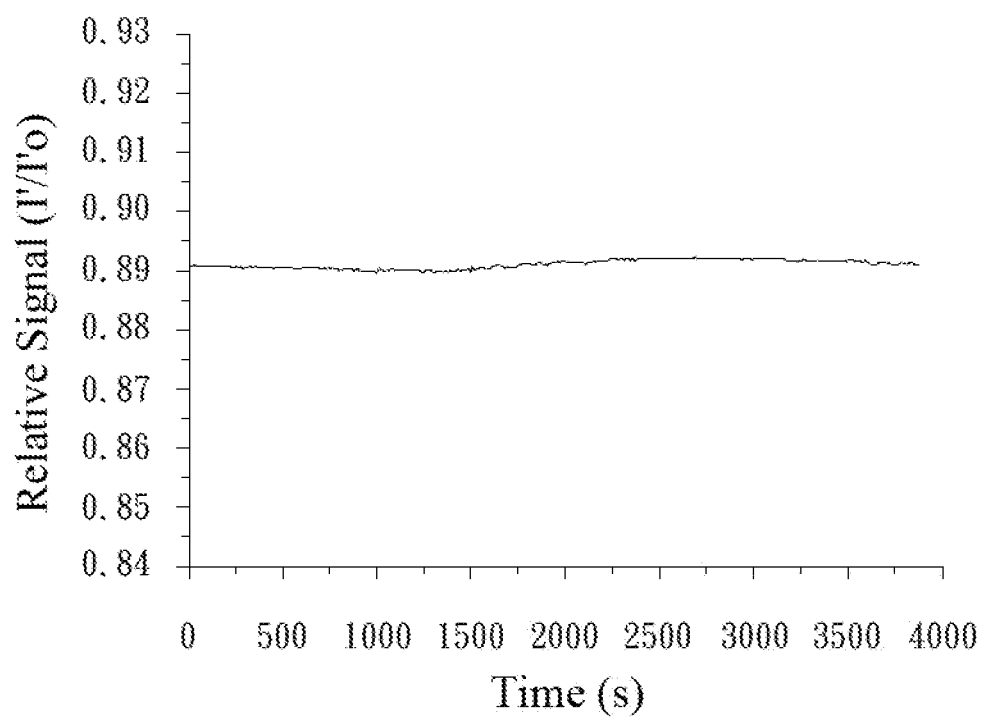
FIG. 8b is a diagram for the relative signal-time relationship obtained by the first embodiment of the self-referencing fiber-optic localized plasmon resonance system according to the present invention.

Refer subsequently to FIG. 8*a*, wherein a diagram for the signal-time relationships obtained by a first embodiment of the self-referencing fiber-optic localized plasmon resonance system according to the present invention is shown. Refer also to FIG. 8*b*, wherein a diagram for the relative signal-time relationship obtained by the first embodiment of the self-referencing fiber-optic localized plasmon resonance system according to the present invention is shown. Due to the sensitivity of the localized plasmon resonance to ambient temperature, the self-referencing fiber-optic localized plasmon resonance sensing system according to the present invention simultaneously performs respective tests on the reference optical fiber 81 and the sensing optical fiber 82 at different temperatures in order to examine the effect on self-correction of temperature fluctuation through the self-referencing operations. In general, the refractive index of a solution relates to temperature; as a result, the signal decreases as temperature arises and vice versa. In the self-referencing fiber-optic localized plasmon resonance sensing system, when temperature increases, the signals in both the reference optical fiber and the sensing optical fiber drop at the same time; while when temperature decreases, however, the signals rise up together; accordingly a relatively flat signal can be seen on the signal versus time diagram acquired after self-referencing by using the relative signal ($I'/I'_0$).

Figure 9A:
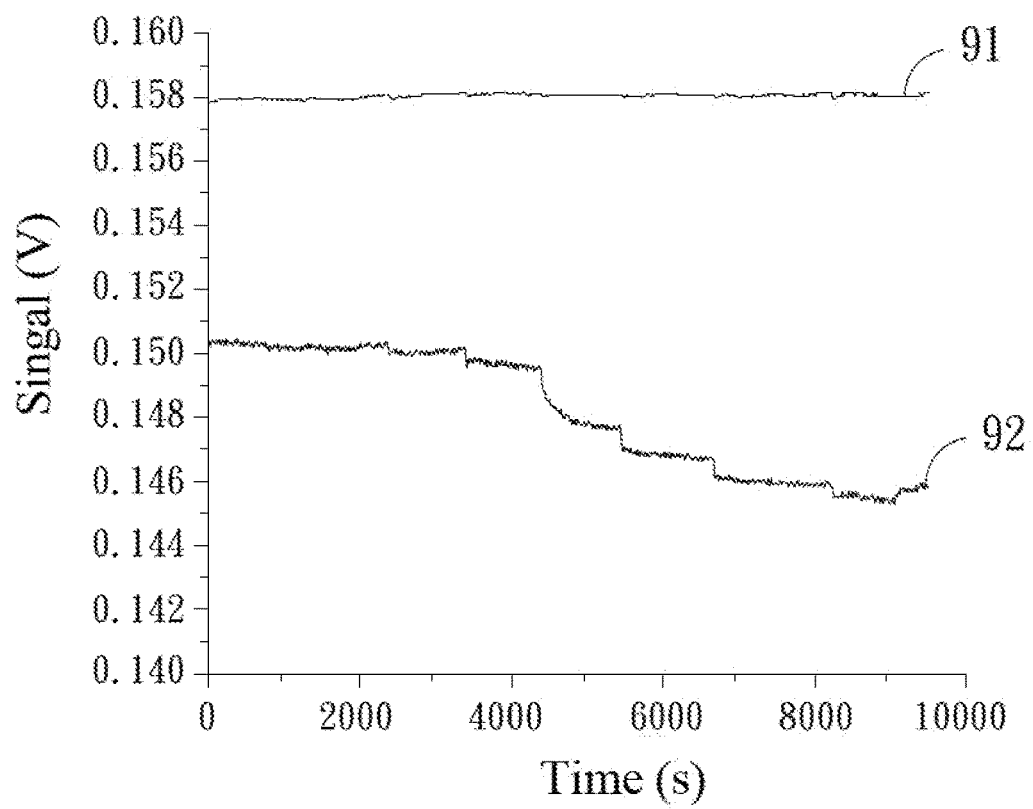
FIG. 9a is a diagram for the signal-time relationships obtained by a second embodiment of the self-referencing fiber-optic localized plasmon resonance system according to the present invention.
Figure 9B:
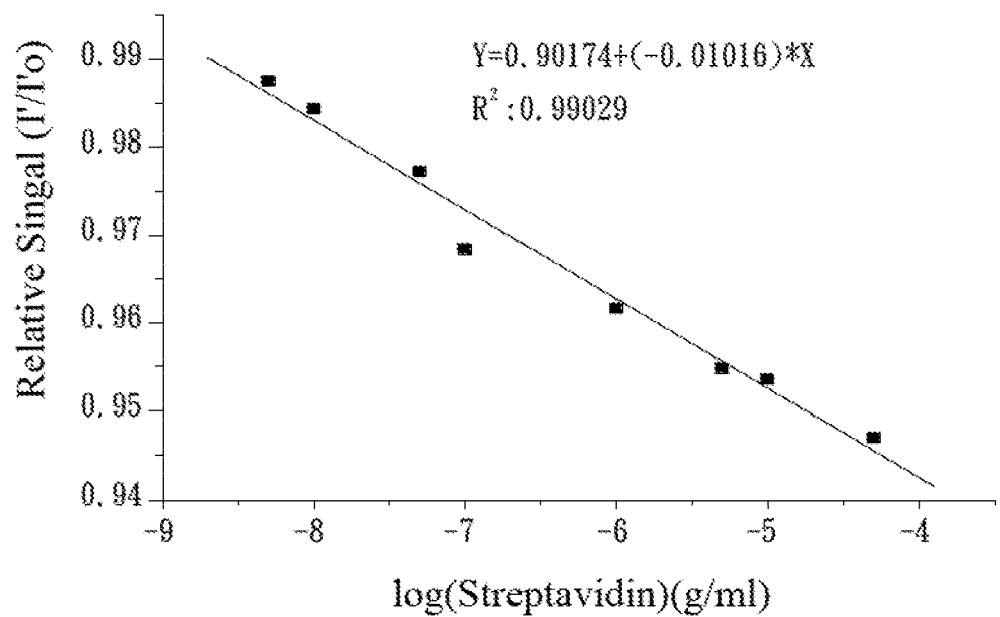
FIG. 9b is a diagram for the plot of relative signal versus logarithm concentration obtained by the second embodiment of the self-referencing fiber-optic localized plasmon resonance system according to the present invention.

Referring to FIG. 9*a*, wherein a diagram of the signal-time relationships obtained by a second embodiment of the self-referencing fiber-optic localized plasmon resonance system according to the present invention is shown. Also referring to FIG. 9*b*, wherein a diagram for the relative signal-logarithm concentration obtained by the second embodiment of the self-referencing fiber-optic localized plasmon resonance system according to the present invention is shown. In order to substantiate the qualitative and quantitative feasibilities for application of the present system, an experiment to detect streptavidin of different concentrations with vitamin H (biotin) as the recognition unit is designed. From the results of the experiment it can be observed that, upon injection of streptavidin at a high concentration, no significant change in signal from the reference optical fiber 91 is shown, essentially because the hydrophility of the hydroxyl end group (—OH) on the surface of the noble metal particles resist nonspecific surface adsorption; meanwhile, when the sensing optical fiber 92 is functionalized with biotin, and upon binding between biotin and streptavidin, a decrease in the signal can be observed (as shown in FIG. 9*a*), and the temporal signal thus generated present a molecular binding kinetic curve. With the above-illustrated results, by means of sequentially injecting streptavidin of different concentrations for tests, the plot of signal versus log concentration has a correlation coefficient of 0.990 (as shown in FIG. 9*b*), which is close to the value of 0.996 obtained from the non self-referencing single fiber-optic sensing system, and the plot also yields a detection limit of $3.8 \times 10^{-11}$ M, which is also similar to the value of $4.1 \times 10^{-11}$ M deduced from the non self-referencing single fiber-optic sensing system.

Figure 10A:
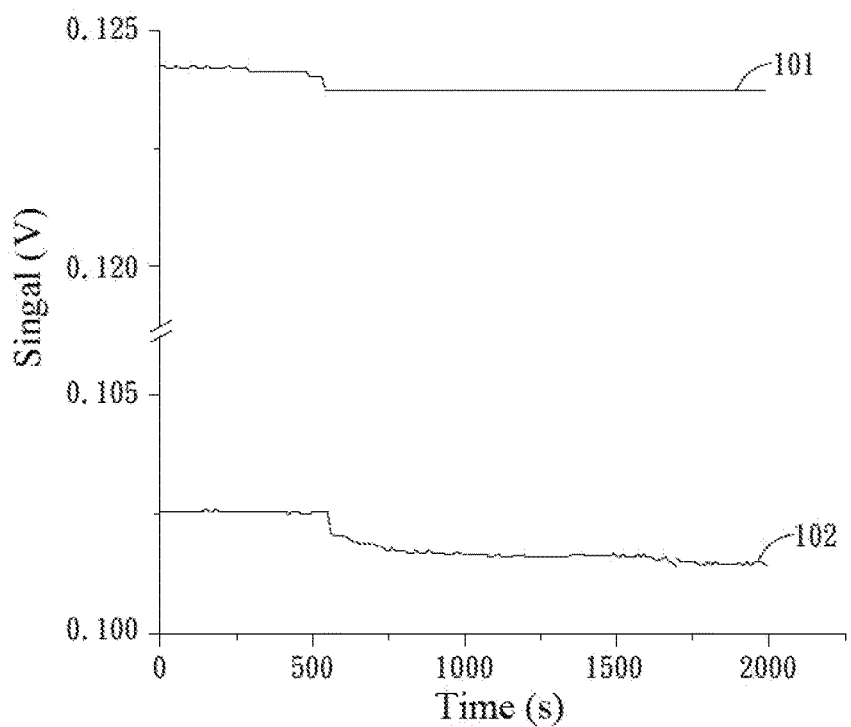
FIG. 10a is a diagram for the signal-time relationships obtained by a third embodiment of the self-referencing fiber-optic localized plasmon resonance system according to the present invention.
Figure 10B:
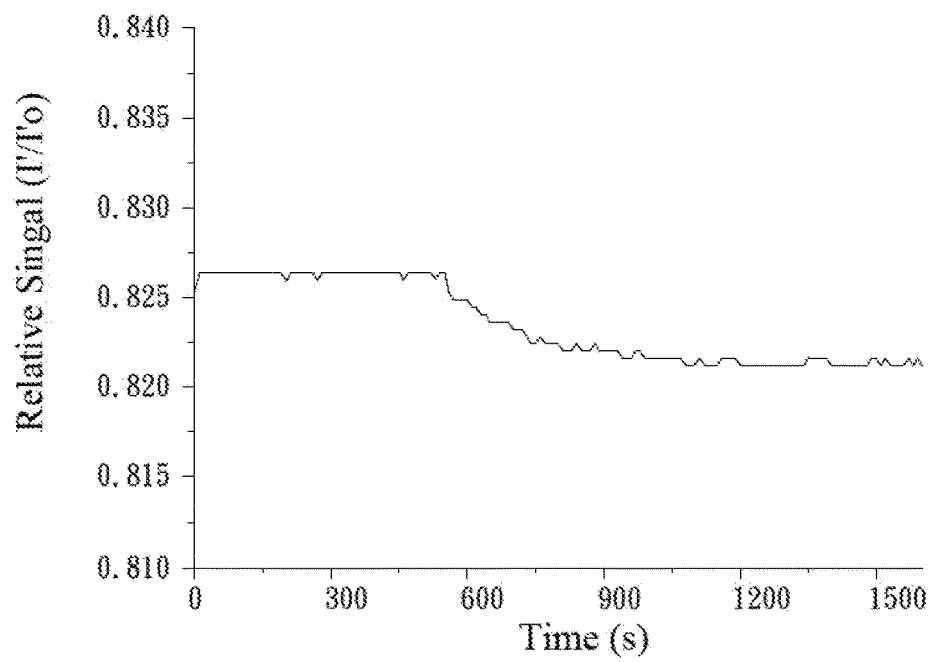
FIG. 10b is a diagram for the relative signal-time relationship obtained by the third embodiment of the self-referencing fiber-optic localized plasmon resonance system according to the present invention.

With reference to FIG. 10*a*, a diagram for the signal-time relationships obtained by a third embodiment of the self-referencing fiber-optic localized plasmon resonance system according to the present invention is shown. Referring to FIG. 10*b* as well, wherein a diagram for the relative signal-time relationship obtained by the third embodiment of the self-referencing fiber-optic localized plasmon resonance system according to the present invention is illustrated. During detection, samples of high viscosity may lead to changes of the refractive index of the solutions, thus resulting in errors during detection. For example, detection of the IL-1β content in the knee synovial fluid of a patient with osteoarthritis (OA) is provided, in which, after sample preparation processes, the sample of synovial fluid still presents comparatively high viscosity. However, by means of the self-referencing sensing system according to the present invention, excessive dilution steps can be avoided for performing the detection, thereby facilitating improvement on the detection limit.

Using a solution of MUA/MCH mixture, it is possible to perform the self-assembly of a mixed monolayer film on the surface of gold nanoparticles. The method of forming the probe includes the steps of, initially, activating the carboxyl end group of MUA, and then conjugating it with an anti-human IL-1β antibody through chemical reactions. In a conventional single fiber-optic sensing system, when detecting a real synovial fluid sample, it is required to dilute the highly viscous sample beforehand, but errors may be so introduced during dilution, causing inaccuracy and unnecessary time cost, and also degrades the detection limit of the method.

However, using the self-referencing fiber-optic localized plasmon resonance sensing system according to the present invention for detection of the real synovial fluid samples, it is possible to start the tests by just slightly diluting the viscous synovial fluid. Since the ultimate goal of the present system is to determine the IL-1β content in the knee synovial fluid of an OA patient, it can be seen that the introduction of a viscous sample causes an initial sharp drop in signals for signals from both the reference optical fiber and the sensing optical fiber (as shown in FIG. 10a), such sharp signal drops are errors and lead to inaccuracy. After self-correction by the self-referencing fiber-optic localized plasmon resonance sensing system, a characteristic molecular binding kinetic curve without the initial sharp drop in signal can be observed (as shown in FIG. 10b), and the measured concentration of IL-1β in the sample is $1.72 \times 10^{-10}$ M, which is close to the result obtained by the single fiber-optic sensing system, but excessive dilution is no longer required.

Figure 11A:
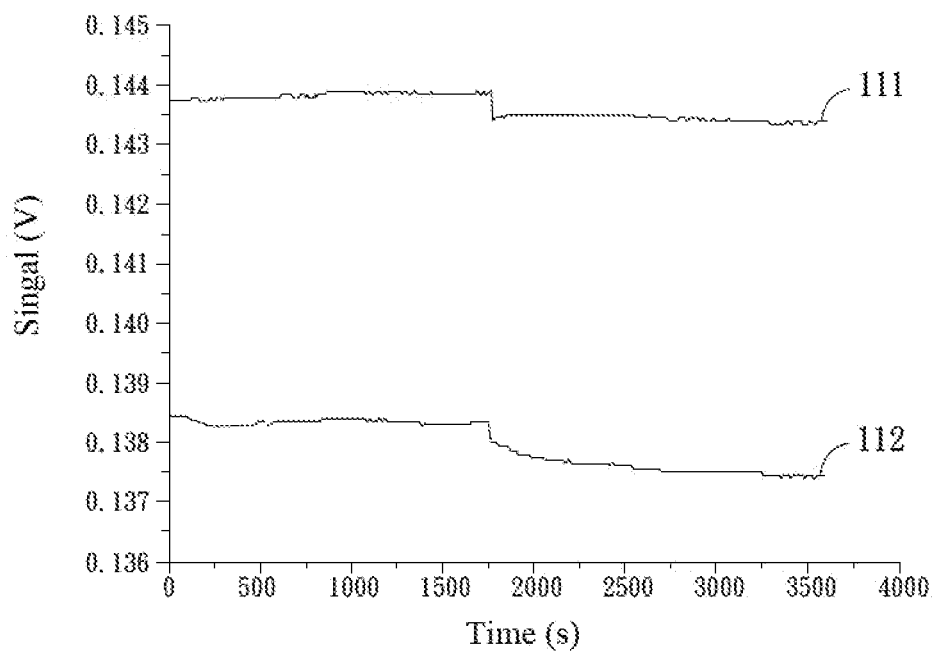
FIG. 11a is a diagram for the signal-time relationships obtained by a fourth embodiment of the self-referencing fiber-optic localized plasmon resonance system according to the present invention.
Figure 11B:
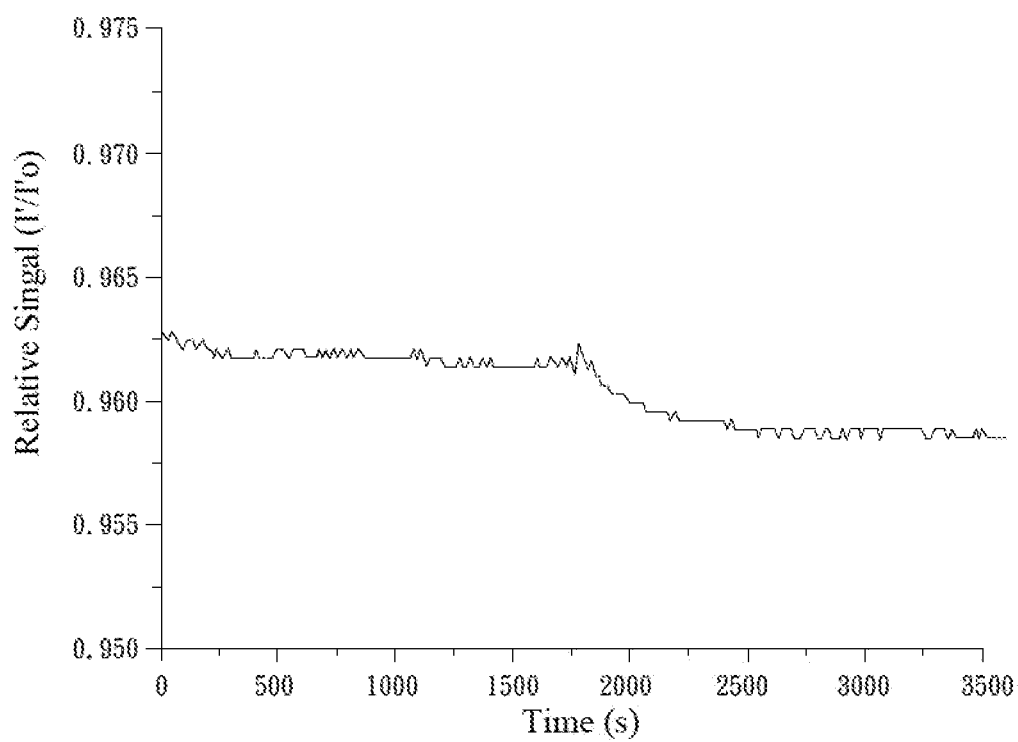
FIG. 11b is a diagram for the relative signal-time relationship obtained by the fourth embodiment of the self-referencing fiber-optic localized plasmon resonance system according to the present invention.

In the following texts, reference is made to FIG. 11a, wherein a diagram for the signal-time relationships obtained by a fourth embodiment of the self-referencing fiber-optic localized plasmon resonance system according to the present invention is shown. Also, referring to FIG. 11b, wherein a diagram for the relative signal-time relationship in the fourth embodiment of the self-referencing fiber-optic localized plasmon resonance system according to the present invention is shown. When a real sample presents a certain color, spectral interference may occur, leading to an error in the analysis. In an experiment using the sap containing CymMV orchid virus, the color of diluted orchid sap is still greenish (absorption band thereof located at about 600 nm), which may cause spectral interference and refractive index difference of the solution as compared to a blank. Upon injecting the sap containing the CymMV virus, since the reference optical fiber is only modified with MCH without the antibody specific for the virus, it can be seen from FIG. 11a that an initial sharp drop in the signal from the reference optical fiber 111, essentially due to the spectral interference and change in refractive index; whereas, the sensing optical fiber 112 is modified on the antibody specific for the virus, thus after the initial sharp drop in the signal, there presents a molecular binding kinetic curve, because of the interaction between the antibody and the virus. With self-correction of signals using signals from both the reference optical fiber 111 and the sensing optical fiber 112 ($I'/I'_0$), it can be clearly seen that the acquired data by self-referencing sensing system as shown in FIG. 11b provides a corrected feature of merely the molecular binding kinetic curve thereby reducing the spectral interference occurring when the sample presents a color.

Figure 12A:
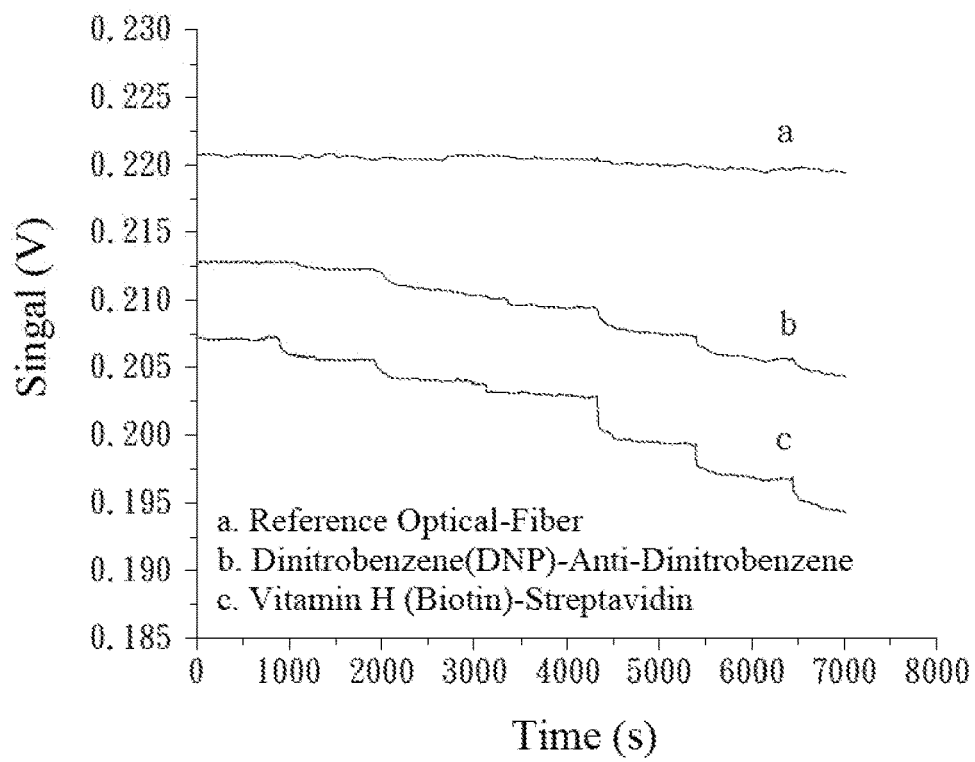
FIG. 12a is a diagram for the signal-time relationships obtained by a fifth embodiment of the self-referencing fiber-optic localized plasmon resonance system according to the present invention.
Figure 12B:
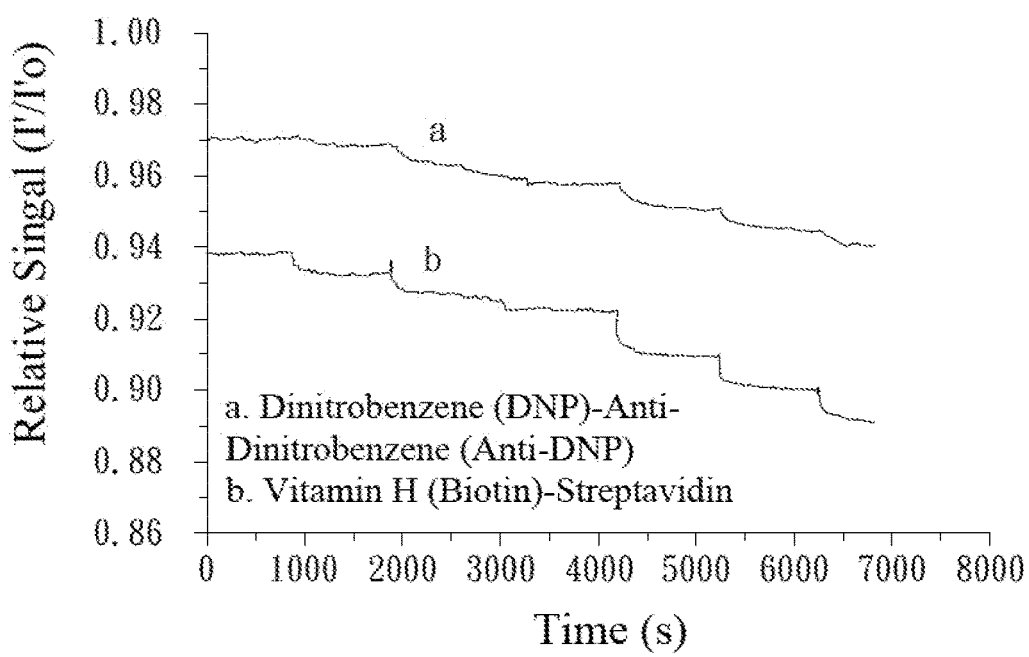
FIG. 12b is a diagram for the relative signal-time relationship obtained by the fifth embodiment of the self-referencing fiber-optic localized plasmon resonance system according to the present invention.

Refer next to FIG. 12a, wherein a diagram for the signal-time relationships obtained by a fifth embodiment of the self-referencing fiber-optic localized plasmon resonance system according to the present invention is shown. Refer subsequently to FIG. 12b, wherein a diagram for the relative signal-time relationship in the fifth embodiment of the self-referencing fiber-optic localized plasmon resonance system according to the present invention. Additionally, refer also to FIG. 12c, wherein a diagram for the relative signal-logarithm concentration relationships in the fifth embodiment of the self-referencing fiber-optic localized plasmon resonance system according to the present invention is shown. Typically, several biochemical species of interest may coexist in a real sample. In order to achieve simultaneous detection of these biochemical species, a component for multiplex detection is designed which is configured with a reference optical fiber without any recognition unit and a plurality of sensing optical fibers modified with one recognition unit for one of the biochemical species on each sensing fiber, thereby allowing simultaneous multiplex detection by using self-referencing.

Figure 12C:
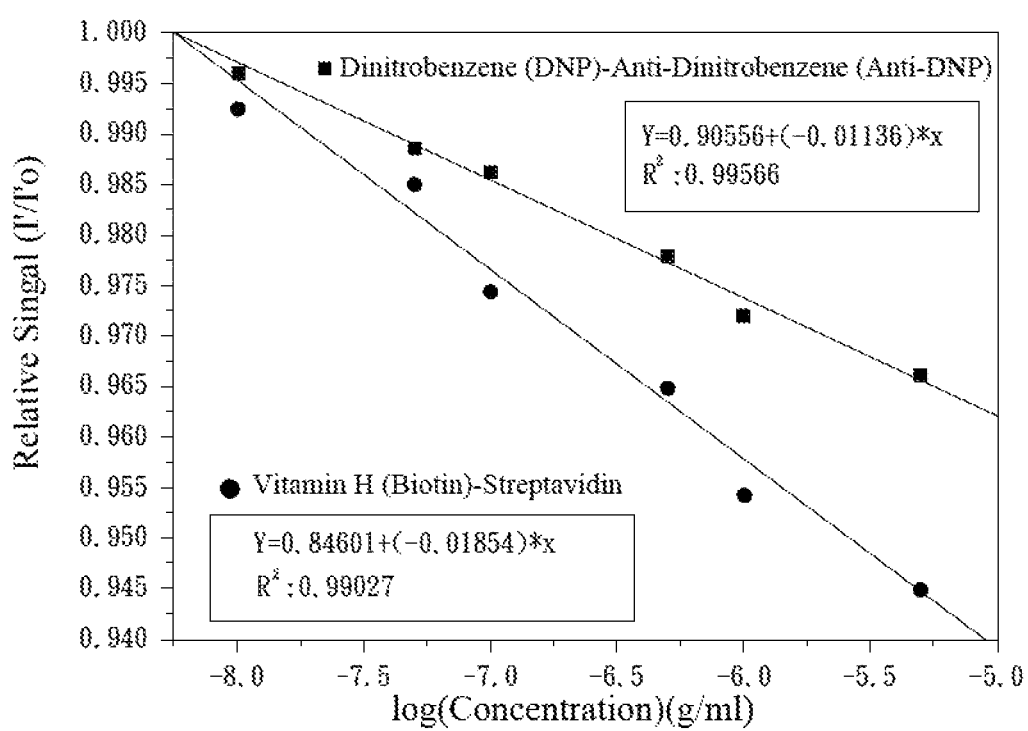
FIG. 12c is a diagram for the plot of relative signal versus logarithm concentration obtained by the fifth embodiment of the self-referencing fiber-optic localized plasmon resonance system according to the present invention.

One experiment for multiplex detection by means of the self-referencing fiber-optic localized plasmon resonance sensing system is to detect the solutions consisting of both streptavidin and anti-dinitrophenyl antibody (anti-DNP) having different concentrations of streptavidin and anti-DNP, and perform self-referencing based on the reference optical fiber in order to achieve multiplex detection. FIG. 12a shows a diagram for the signal-time relationships from the reference optical fiber and the sensing optical fibers. It can be seen that the molecular binding kinetic curves for detection of streptavidin by the biotin-functionalized optical fiber and detection of anti-DNP by the DNP-functionalized optical fiber at different concentrations are observed. With self-correction of signals using signals from the reference optical fiber 111 and the sensing optical fibers, it can be seen that as the concentration of the targets increases, the characteristic molecular binding kinetic curves and linear calibration graphs are still observed, which substantiates the feasibility of the self-referencing simultaneous multiplex detection, as shown in FIGS. 12b and 12c.

However, the reference optical fiber and the sensing optical fiber is configured to be the example, the present disclosure shall be not limited thereto. Actually, the self-referencing fiber-optic localized plasmon resonance sensing device may be one example of the self-referencing localized plasmon resonance sensing device, the reference optical fiber may be one example of the reference optical waveguide element, and the sensing optical fiber may be one example of the sensing optical waveguide element. The optical waveguide element may be selected from one of the following: optical fiber, channel waveguide, planar waveguide, or tubular waveguide.

Figure 13:
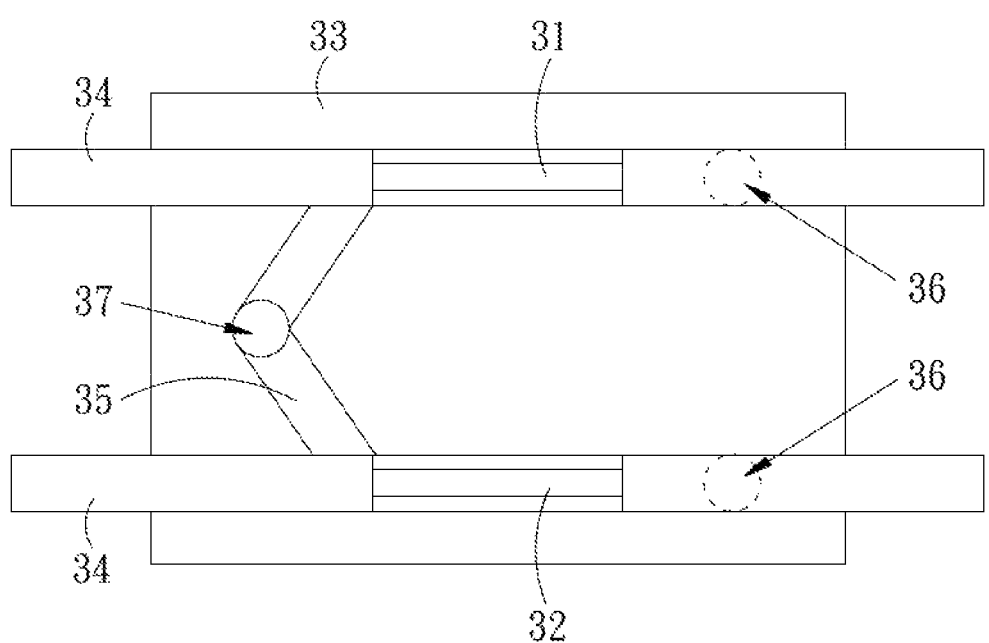
FIG. 13 is a diagram for a self-referencing localized plasmon resonance sensing device according to the sixth embodiment of the present invention.

Refer now to FIG. 13, wherein a diagram for a self-referencing localized plasmon resonance sensing device according to the sixth embodiment of the present invention is shown. The calibration slopes of the reference optical waveguide element 31 and the sensing optical waveguide element 32 of the sixth embodiment may be different. The processing unit 74, which may be the processor, utilizes the difference between the signal generated by the sensing optical waveguide element 32 and the signal generated by the reference optical waveguide element 31 to obtain the sensor response. Here, the other element of the self-referencing localized plasmon resonance sensing device and system thereof in the other embodiments can be existed in the sixth embodiment. Besides, the material of the element of the other embodiments can be utilized in the element of the sixth embodiment.

For more details, the self-referencing localized plasmon resonance sensing device of the sixth embodiment comprises a reference optical waveguide element 31, a sensing optical waveguide element 32, and a carrier 33. The carrier 33 places the reference optical waveguide element 31 and the sensing optical waveguide element 32. Here, the carrier 33 has channels 34 for placing the reference optical waveguide element 31 and the sensing optical waveguide element 32. Besides, the carrier has a V-shape channel 35 connected to the channels 34 for injecting the sample into the channels 34. Here, an opening 37 is formed on the top of the V-shape channel 35 for injecting the sample into the V-shape channel 35, two end of the V-shape channel 35 are respectively connected to the channels 34 for guiding the sample from the V-shape channel 35 into the channels 34. Here, the channels 34 have openings 36 respectively corresponding to the reference optical waveguide element 31 and the sensing optical waveguide element 32 for flowing out the sample. Besides, the reference optical waveguide element 31 is modified with a first noble metal nanoparticle layer. Part of an incident light, which is emitted from the light source 71, is guided into the reference optical waveguide element 31 to generate the first localized plasmon resonance sensor signal. Here, the reference optical waveguide element 31 has a first calibration slope. The first localized plasmon resonance sensor signal includes the first signal generated by detecting the blank with the reference optical waveguide element 31 and the second signal generated by detecting the sample with the reference optical waveguide element 31.

Besides, the sensing optical waveguide element 32 is modified with a second noble metal nanoparticle layer. The second noble metal nanoparticle layer is further modified with the recognition unit. Here, the recognition unit can comprise a chemical recognition molecule, an antibody, an antigen, a lectin, a hormone receptor, a nucleic acid or a carbohydrate. The other part of the incident light, which is emitted from the light source 71, is guided into the sensing optical waveguide element 32 to generate the second localized plasmon resonance sensor signal. Here, the sensing optical waveguide element 32 has a second calibration slope, which may be different from the first calibration slope of the reference optical waveguide element 31. The second localized plasmon resonance sensor signal includes the third signal generated by detecting the blank with the sensing optical waveguide element 32 and the fourth signal generated by detecting the sample with the sensing optical waveguide element 32. Here, the respective number of the reference optical waveguide element 31 and the sensing optical waveguide element 32 is one or more.

The photodetecting unit 73, such as the composition of at least one photodiode, receives the first localized plasmon resonance sensor signal and the second localized plasmon resonance sensor signal generated by the reference optical waveguide element 31 and the sensing optical waveguide element 32, respectively. The photodetecting unit 73 then transmits the first localized plasmon resonance sensor signal and the second localized plasmon resonance sensor signal to the processing unit 74, which may be the processor. The processing unit 74 normalizes the first difference between the second signal and the first signal, and normalizes a second difference between the fourth signal and the third signal. Then, the processing unit 74 utilizes the first calibration slope of the reference optical waveguide element 31 and the second calibration slope of the sensing optical waveguide element 32 to regulate the second difference, which is normalized. Thereby, a regulated second difference can be obtained. Afterward, the processing unit 74 utilizes the difference between the first difference, which is normalized, and the regulated second difference to obtain the sensor response. Hence, an easy and more accurate compensation of thermal and bulk-composition effects as well as nonspecific adsorption can be allowed. Besides, the property of the reference optical waveguide element 31 and the sensing optical waveguide element 32 can be different.

For example, the localized plasmon resonance sensing technique used in the present invention is based on the absorption of evanescent wave by a noble metal nanoparticle layer on the optical waveguide element. When light propagates along the optical waveguide element by consecutive total internal reflection (TIR), the noble metal nanoparticle are excited by the evanescent field and thus the light transmitted through the optical waveguide element is attenuated by interaction with the noble metal nanoparticle. As the attenuation is enhanced by multiple TIRs, the low absorbance of the noble metal nanoparticle layer can be significantly enhanced. Because this localized plasmon resonance sensing technique is based on the absorbance change of the noble metal nanoparticle layer at different refractive index (RI) environments, we assume the bulk absorption coefficient of the noble metal nanoparticle layer will increase from $\alpha_0$ in a blank to $\alpha_0+\Delta\alpha$ in a sample when the medium RI surrounding the noble metal nanoparticle layer increases by $\Delta n$. As a result, if we plot $\Delta\alpha/\alpha_0$ versus $\Delta n$, a linear regression line with a slope m will be obtained. Since the localized plasmon resonance sensor response can be approximated by the following relationship: $\Delta I/I_0=(I_0-I)/I_0=1-I/I_0 \approx \Delta\alpha/\alpha_0$, where the normalized response, $\Delta I/I_0$, is defined as the collected signal intensity from a noble metal nanoparticle layer-modified optical waveguide element immersed in a sample (I) to that of the same optical waveguide element immersed in a blank ($I_0$), a plot of $\Delta I/I_0$ versus $\Delta n$ will also yield a linear regression line with a slope m. Since molecular binding on the noble metal nanoparticle surface will induce an increase of local RI within the sensing depth of the noble metal nanoparticle, the binding will result in a decrease in transmitted light intensity through the optical waveguide element. Therefore, with a recognition molecule conjugated on the noble metal nanoparticle surface, a corresponding analyte can be detected in real-time without the use of a label.

Thermal and bulk-composition effects can generate significant changes in the localized plasmon resonance sensor response, which may obscure those caused by specific binding of the analyte. Here, a novel self-referencing mechanism in a dual-channel localized plasmon resonance sensing system is utilized to compensate those effects (thermal, bulk refractive index, and color interferences) in complex samples. The sensing optical waveguide element 32 with immobilization of a specific recognition molecule, will measure specific binding of an analyte as well as undesirable thermal and bulk-composition effects. Ideally, there should be no nonspecific adsorption at the sensing optical waveguide element 32. However, in reality, nonspecific adsorption is difficult to be avoided completely. As such, the compensated response can be described by the following relationship:

$$\frac{\Delta I_S}{I_{S0}} = m_S \times (\Delta n_M + \Delta n_{NA} + \Delta n_{SA}) \qquad (1)$$

where $\Delta I_S/I_{S0}$ is the normalized response of the sensing optical waveguide element 32, $m_S$ is the calibration slope of the sensing optical waveguide element 32, $\Delta n_M$ is the change of bulk RI of the medium, $\Delta n_{NA}$ is the change of effective local RI due to nonspecific adsorption, if any, and $\Delta n_{SA}$ is the change of effective local RI due to specific adsorption.

Besides, the reference optical waveguide element 31 without immobilization of a specific recognition molecule, will only measure the thermal and bulk-composition effects and nonspecific binding, if any, and the sensor response can be described by the following relationship:

$$\frac{\Delta I_R}{I_{R0}} = m_R \times (\Delta n_m + \Delta n_{NA}) \qquad (2)$$

where $\Delta I_R/I_{R0}$ is the normalized response of the reference optical waveguide element 31 and $m_R$ is the calibration slope of the reference optical waveguide element 31.

Rearranging Equation (1), the sensor response due to specific adsorption only is:

$$\frac{\Delta I_{S,SA}}{I_{S0}} = m_s \times \Delta n_{SA} = \frac{\Delta I_S}{I_{S0}} - m_S \times (\Delta n_M + \Delta n_{NA}) \quad (3)$$

Ideally, if the calibration slope of the sensing optical waveguide element 32 equals to the calibration slope of the reference optical waveguide element 31, namely, $m_S=m_R$, from Equations (2) and (3), $$\frac{\Delta I_{S,SA}}{I_{S0}} = m_s \times \Delta n_{SA} = \frac{\Delta I_S}{I_{S0}} - \frac{\Delta I_R}{I_{R0}} \quad (4)$$

However, it is very tedious and costly to follow a strict quality control scheme in order to control the surface coverage of the noble metal nanoparticle on the waveguide surface and $\alpha_0$ and hence the calibration slope of the sensing optical waveguide element 32 and the reference optical waveguide element 31 to be exactly the same.

If the calibration slope of the sensing optical waveguide element 32 is different from the calibration slope of the reference optical waveguide element 31, namely, $m_S \neq m_R$, from Equations (2) and (3), $$\frac{\Delta I_{S,SA}}{I_{S0}} = \frac{\Delta I_S}{I_{S0}} - \frac{m_S}{m_R} \times \frac{\Delta I_R}{I_{R0}} \quad (5)$$

When the injection of a sample causes a change of medium RI, $\Delta n_M$, the normalized responses of the sensing optical waveguide element 32 and the reference optical waveguide element 31 will be $\Delta I_{S,M}/I_{S0}$ and $\Delta I_{R,M}/I_{R0}$, respectively. Both these changes can be easily interrogated from the sensorgrams. As the plots of $\Delta I_{S,M}/I_{S0}$ and $\Delta I_{R,M}/I_{R0}$ versus $\Delta n_M$ represent the calibration slopes of the sensing optical waveguide element 32 and the reference optical waveguide element 31, respectively, Equation (5) can be rewritten as:

$$\frac{\Delta I_{S,SA}}{I_{S0}} = \frac{\Delta I_S}{I_{S0}} - \frac{\Delta I_{S,M}/I_{S0}}{\Delta I_{R,M}/I_{R0}} \times \frac{\Delta I_R}{I_{R0}} \quad (6)$$

This is an interesting result implying that the intentional use of a blank and a sample with different RI values will allow an easy and more accurate compensation of thermal and bulk-composition effects as well as nonspecific adsorption.

Figure 14:
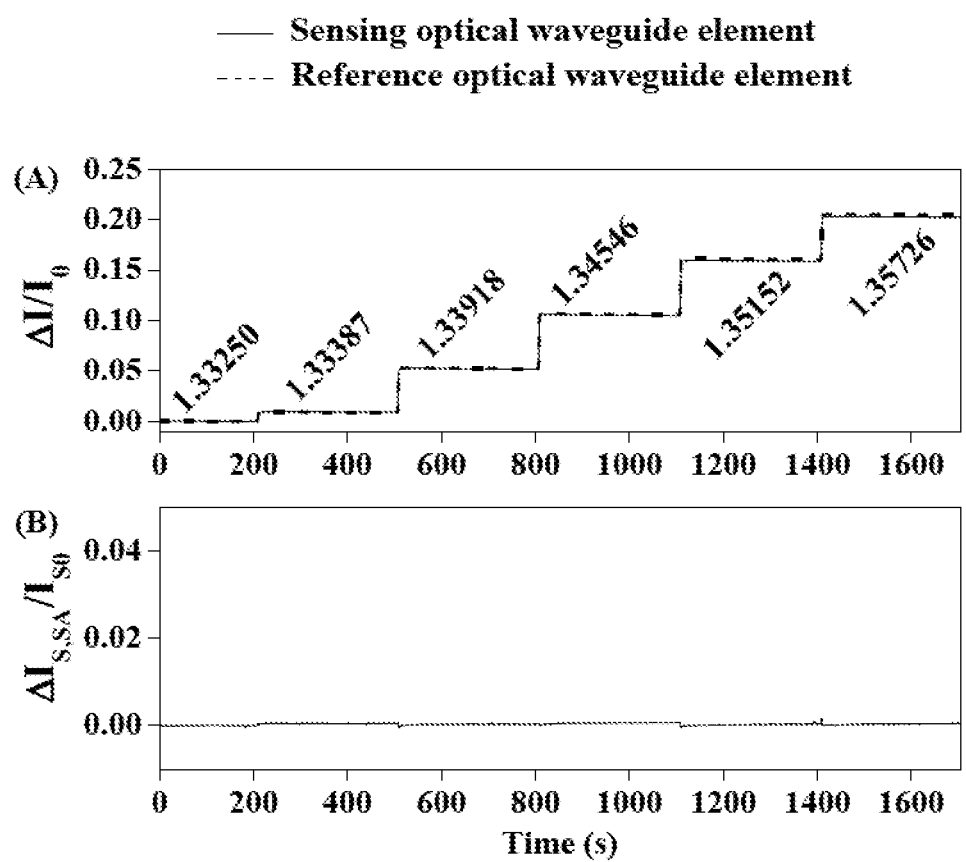
FIG. 14 illustrates the quantification of the sensor responses of the self-referencing localized plasmon resonance sensing system to bulk RI variations, ultrapure water and phosphate buffered saline (PBS) solutions with different refractive indexes being successively injected into a sensor chip, wherein (A) shows representative sensorgrams of the normalized responses of both the sensing optical waveguide element and the reference optical waveguide element; (B) shows the compensated response obtained by the sensing system.

To quantify the sensor responses of the self-referencing localized plasmon resonance sensing system to bulk RI variations, ultrapure water and phosphate buffered saline (PBS) solutions with different refractive indexes (1.33250-1.35726) were successively injected into a sensor chip. Referring to part (A) of FIG. 14, which shows representative sensorgrams of the normalized responses of both the sensing optical waveguide element and the reference optical waveguide element. The baselines were established as both optical waveguide elements were in contact with ultrapure water. From the baseline of the sensing optical waveguide element, the power stability or the relative standard deviation of the noise ($\sigma$) is estimated to be 0.0073% per 120 second. Including the noises due to five injections of ultrapure water samples, the sum of squared residuals (SSE) about regression of the normalized response of the sensing optical waveguide element is estimated to be 0.0319%. With the stepwise increase of RI of the injected samples, the normalized responses of both optical waveguide elements show step-up trends. Through correction by Equation (5), the compensated response ideally should be a straight line with a mean of about zero. Referring to part (B) of FIG. 14, which shows the compensated response obtained by the sensing system. As shown in part (B) of FIG. 14, the SSE about regression of the compensated response is estimated to be 0.0151%. The comparable and even better SSE values indicate that the self-referencing localized plasmon resonance sensing system effectively compensate background RI variations.

Figure 15:
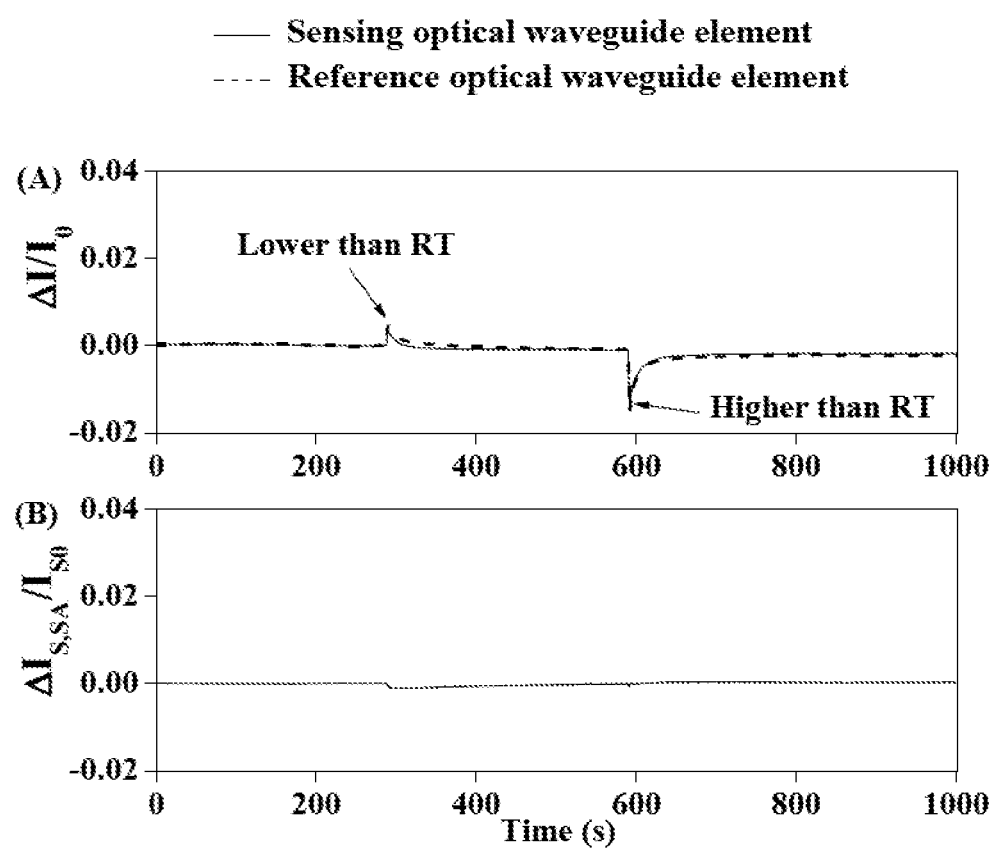
FIG. 15 illustrates the compensation of the temperature effect by using the self-referencing localized plasmon resonance sensing device and the system thereof of the present invention, wherein (A) illustrates real-time normalized responses of the sensing optical waveguide element and the reference optical waveguide element in water in response to injection of ultrapure water samples at about 15° C. and 45° C. in the self-referencing localized plasmon resonance sensing system; (B) shows the compensated response obtained by the sensing system in response to temperature changes.

Further, the temperature effect is compensation by using the self-referencing localized plasmon resonance sensing device and the system thereof of the present invention. In general, the refractive index of a solution relates to temperature. It has been found that a change in temperature causes a change in the RI of water by about $9 \times 10^{-5}$ RIU·°C.$^{-1}$ at a wavelength of 632.8 nm. Referring to part (A) of FIG. 15, which illustrates real-time normalized responses of the sensing optical waveguide element and the reference optical waveguide element in water in response to injection of ultrapure water samples at about 15° C. and 45° C. In the self-referencing localized plasmon resonance sensing system, when temperature decreases, the normalized responses of both optical waveguide elements rise at the same time; while when temperature increases, the normalized responses of both optical waveguide elements fall at the same time. From the data shown in part (A) of FIG. 15, the SSE about regression of the normalized response of the sensing optical waveguide element to include the temperature effect is estimated to be 0.2316%. Besides, referring to part (B) of FIG. 15, which shows the compensated response obtained by the sensing system in response to temperature changes. As shown in part (B) of FIG. 15, the SSE about regression of the compensated response is estimated to be 0.0284%. Such a result indicates that the self-referencing localized plasmon resonance sensing system provides excellent compensation for temperature variation. On the other hand, compensation of temperature change in surface plasmon resonance (SPR) sensors is challenging.

Figure 16:
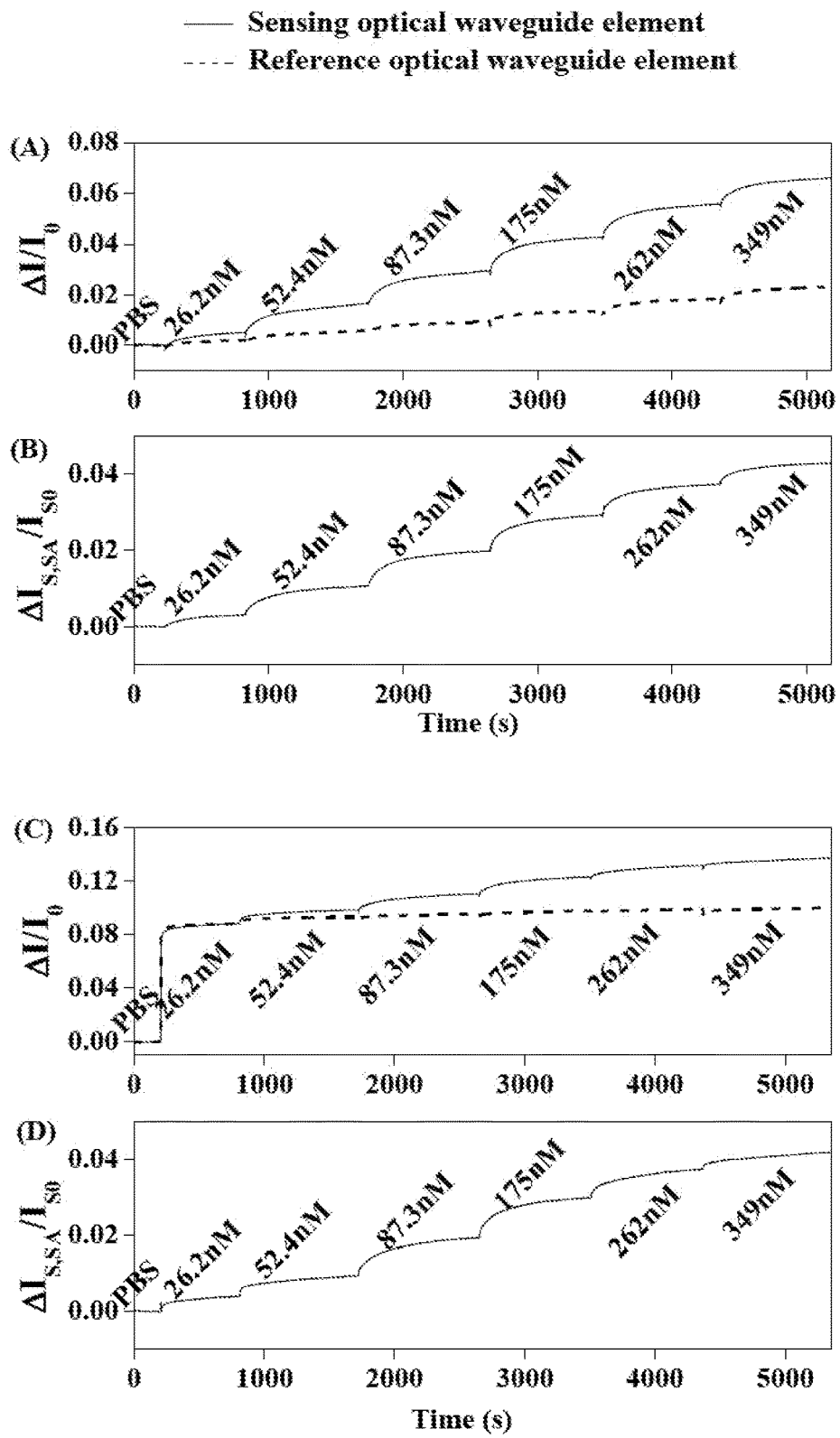
FIG. 16 illustrates the compensation of the nonspecific adsorption effect by using the self-referencing localized plasmon resonance sensing device and the system thereof of the present invention, wherein (A) shows the data for both the reference optical waveguide element and the sensing optical waveguide element during sequential exposure of both waveguide elements to various samples of anti-biotin dissolved in PBS buffer with increasing concentration from 26.2 nM to 349 nM; (B) shows the compensated response obtained by the self-referencing sensing system of the sixth embodiment of the present invention; (C) shows a 1×PBS solution was injected into a sensor chip to establish flat baselines, and then various samples of erythrosine ($4 \times 10^{-5}$ g/mL) dissolved in 10×PBS buffer and spiked with increasing concentration of anti-biotin from 26.2 nM to 349 nM being sequentially injected into the sensor chip; (D) shows the compensated sensor response of the sixth embodiment of the present invention.
Figure 17:
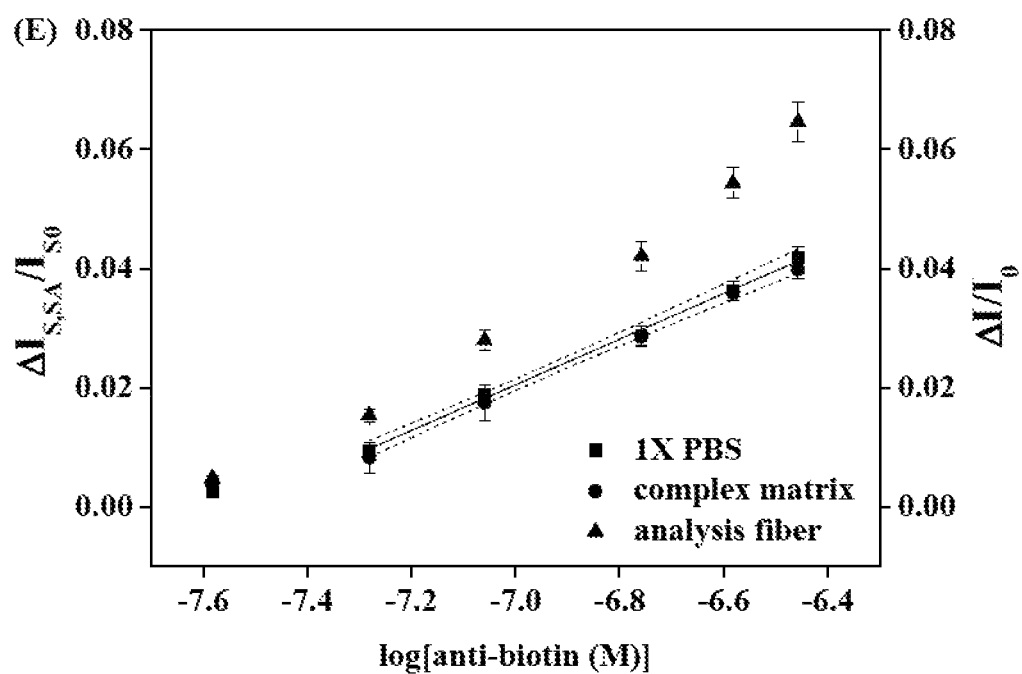
FIG. 17 shows the calibration graphs of anti-biotin obtained by the self-referencing sensing system of the sixth embodiment of the present invention.

Besides, the nonspecific adsorption effect is compensation by using the self-referencing localized plasmon resonance sensing device and the system thereof of the present invention. For biosensor application in real samples, nonspecific adsorption will lead to error in biosensors based on detection of RI change near the biosensor surface. Although various approaches have been employed to minimize nonspecific adsorption at sensor surfaces, it is still technology challenging to completely eliminate this effect. An alternative is through compensation of nonspecific adsorption effect by the mechanism of the reference sensor. If the reference sensor is identical except without a functionalized recognition molecule, the reference sensor can be used to compensate for nonspecific adsorption. Referring to part (A) of FIG. 16, which shows the data for both the reference optical waveguide element 31 and the sensing optical waveguide element 32 during sequential exposure of both waveguide elements to various samples of anti-biotin dissolved in PBS buffer with increasing concentration from 26.2 nM to 349 nM. As shown in part (A) of FIG. 16, there is a little nonspecific adsorption on the reference optical waveguide element 31 while the sensing optical waveguide element 32 yields larger signals. Referring to part (B) of FIG. 16, which shows the compensated response obtained by the self-referencing sensing system of the sixth embodiment. By Equation (4), the compensated response is calculated via the pair-wise differences of normalized responses between the waveguide elements. Referring to FIG. 17, which shows the calibration graphs of anti-biotin obtained by the self-referencing sensing system of the sixth embodiment. As shown in FIG. 17, the calibration graph of $\Delta I_{S,SA}/I_{S0}$ versus log anti-biotin concentration is linear in the concentration range between 52.4 nM to 349 nM (correlation coefficient, r=0.9989, n=3). The limit of detection (LOD) of the self-referencing localized plasmon resonance sensing system for anti-biotin is estimated to be 29.5 nM. On the other hand, if only the normalized response from the sensing optical waveguide element 32 is used to establish the calibration graph, the error could be as large as 46%.

Besides, both bulk refractive index and nonspecific adsorption effects are compensation by using the self-referencing localized plasmon resonance sensing device and the system thereof of the present invention. In the example, the RIs of the buffers used to establish the baselines and to dissolve the samples are intentionally chosen to be different in order to demonstrate the feasibility of compensation for both the bulk refractive index effect and the nonspecific adsorption effect and also to take advantage of the sharp responses to RI change by the two optical waveguide sensors to correct for the difference in calibration slopes between the reference optical waveguide element 31 while the sensing optical waveguide element 32. Referring to part (A) of FIG. 18, which shows real-time normalized responses of the sensing optical waveguide element 32 and the reference optical waveguide element 31 upon injection of an anti-biotin sample with a concentration of 52.4 nM in 5×PBS (RI=1.33918). As shown in part (A) of FIG. 18, the normalized responses of both the sensing optical waveguide element 32 and the reference optical waveguide element 31 increase immediately and simultaneously due to the increase in RI. Then the normalized response of the sensing optical waveguide element 32 continues to increase and follow a molecular binding kinetic curve while the normalized response of the reference optical waveguide element 31 increases very slowly due to nonspecific adsorption. The normalized responses due to matrix change, $\Delta I_{S,M}/I_{S0}$ and $\Delta I_{R,M}/I_{R0}$ can be easily determined by estimation of $\Delta I_{S,M}$ and $\Delta I_{R,M}$ using the intersection points of the molecular binding kinetic curve and the response curve due to bulk RI change.

Figure 18:
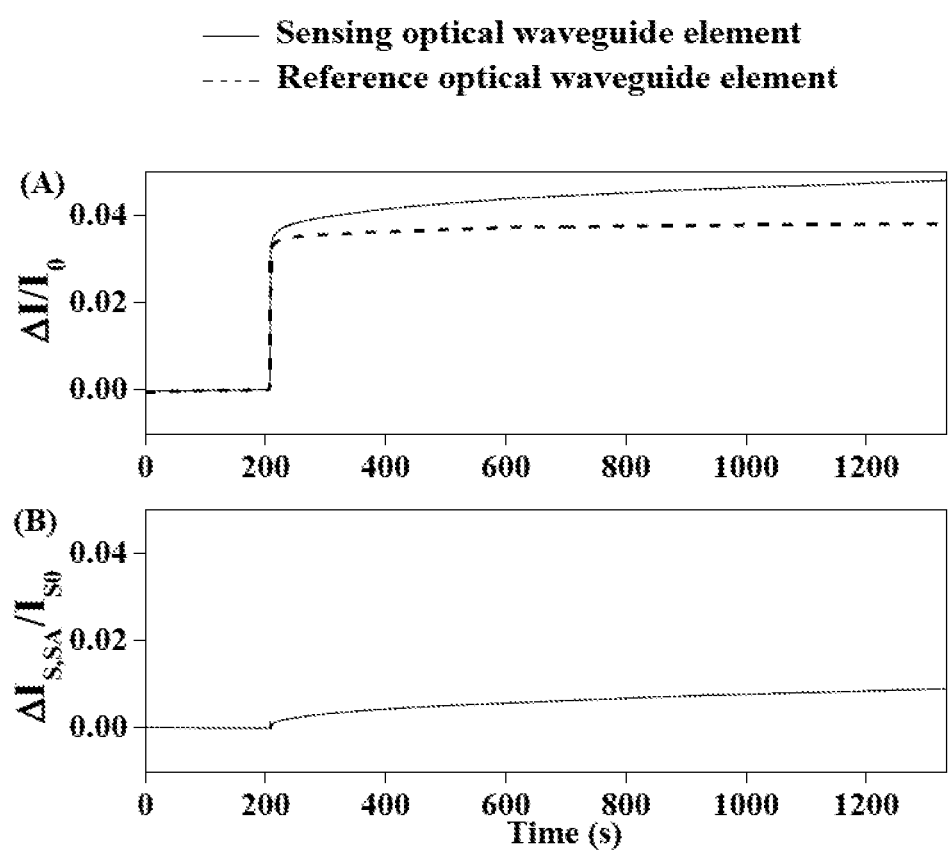
FIG. 18 illustrates the compensation of both refractive index and nonspecific adsorption effects by using the self-referencing localized plasmon resonance sensing device and the system thereof of the present invention, wherein (A) shows real-time normalized responses of the sensing optical waveguide element and the reference optical waveguide element upon injection of an anti-biotin sample with a concentration of 52.4 nM in 5×PBS (RI=1.33918); (B) shows the compensated response obtained by the self-referencing sensing system of the sixth embodiment of the present invention.

Continued speaking, referring to part (B) of FIG. 18, which shows the compensated response obtained by the self-referencing sensing system of the sixth embodiment of the present invention. As shown in FIG. 18, as the regions of sharp rise in normalized responses provide a mechanism to correct for the difference in calibration slopes between the sensing optical waveguide element 32 and the reference optical waveguide element 31, the compensated response can be calculated by Equation (6). From the calibration graph as shown in part (B) of FIG. 18, the concentration of anti-biotin in the spiked sample was estimated to be 54.1±4.0 nM (n=3), yielding a percent recovery of 103.2%. Such a result indicates that the self-referencing localized plasmon resonance sensing system provides excellent compensation for both the bulk refractive index effect and the nonspecific adsorption effect in a sample.

Besides, the color interference is compensation by using the self-referencing localized plasmon resonance sensing device and the system thereof of the present invention. Referring to part (A) of FIG. 19, which shows the extinction spectra of an erythrosine solution and a noble metal nanoparticle layer on the reflecting surface of an optical waveguide element obtained by in-line transmission. As shown in part (A) of FIG. 19, when a real sample has a color overlapping with the excitation spectrum of the incident light, the evanescent wave at the reflecting surface of the waveguide element may be absorbed by the matrix of the real sample as well as by the noble metal nanoparticle. Consequently, spectral interference will occur and lead to error in the analysis. In the example of the present invention, a color matrix is intentionally made by adding a dye, erythrosine, in the sample. Obviously, the peak wavelength of a solution of erythrosine ($2\times10^{-5}$ g/mL) at about 527 nm is overlapping with the peak emission wavelength of the LED used in this example, and is also overlapping with the plasmon absorption band of the noble metal nanoparticle layer.

Figure 19:
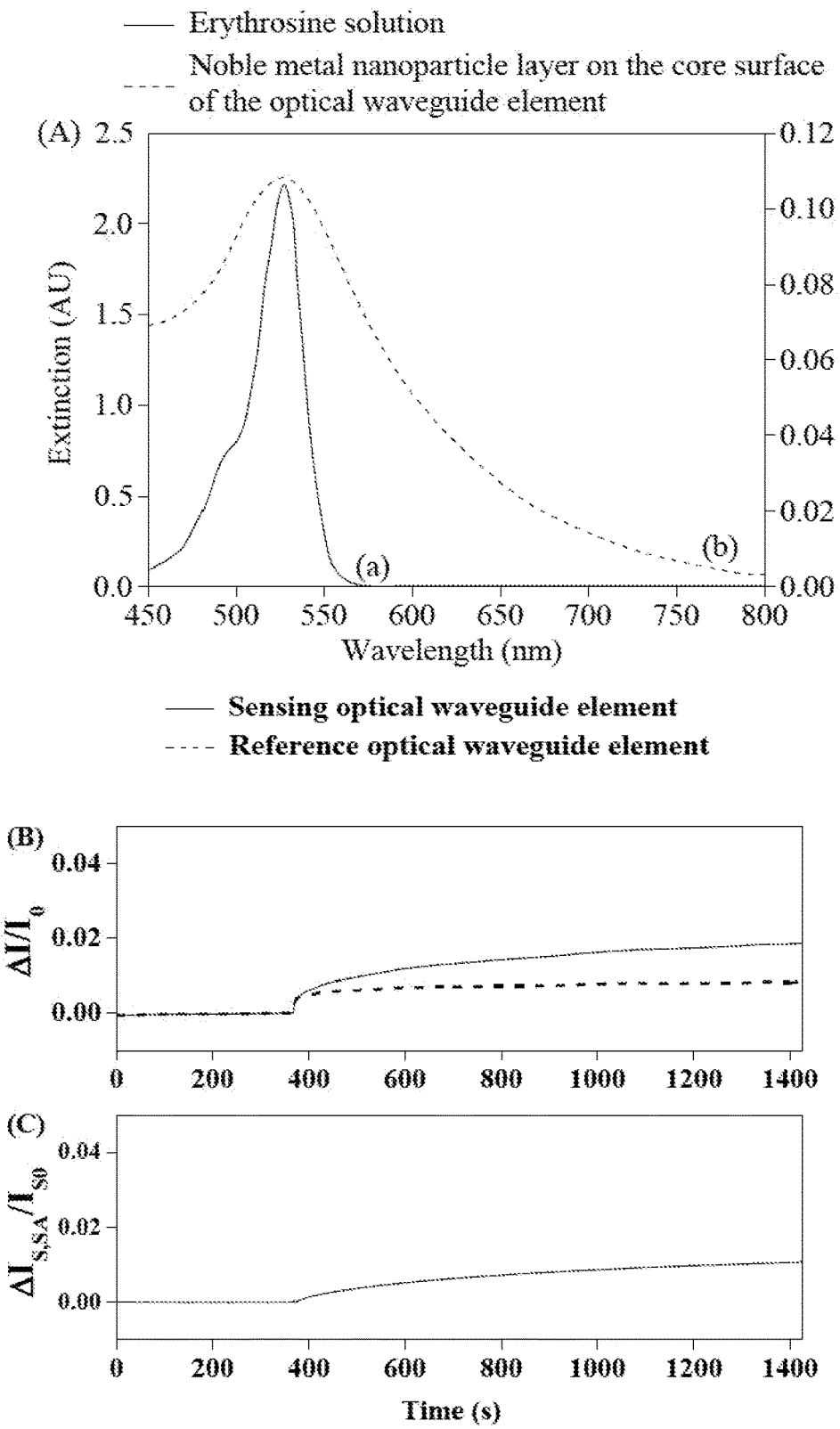
FIG. 19 illustrates the compensation of the color interference by using the self-referencing localized plasmon resonance sensing device and the system thereof of the present invention, wherein (A) shows the extinction spectra of an erythrosine solution and a noble metal nanoparticle layer on the reflecting surface of an optical waveguide element obtained by in-line transmission; (B) shows the real-time normalized response of the optical waveguides upon injection of an anti-biotin sample with a concentration of 52.4 nM in erythrosine solution; (C) shows the compensated response obtained by the self-referencing sensing system of the sixth embodiment of the present invention.

Referring to parts (B) and (C) of FIG. 19, which show the real-time normalized response of the optical waveguides upon injection of an anti-biotin sample with a concentration of 52.4 nM in erythrosine solution, and the compensated response obtained by the self-referencing sensing system of the sixth embodiment of the present invention, respectively. As shown in parts (B) and (C) of FIG. 19, the normalized responses of both the sensing optical waveguide element 32 and the reference optical waveguide element 31 increase immediately and simultaneously due to the color interference when an erythrosine solution spiked with anti-biotin (52.4 nM) was injected into the sensor chip. On the other hand, after the sharp rise in signal, the normalized response of the sensing optical waveguide element 32 continues to increase and follow a molecular binding kinetic curve while the normalized response of the reference optical waveguide element 31 increases very slowly due to nonspecific adsorption. By the same rationale, the compensated sensor response can be calculated by Equation (6). From the calibration graph as shown in FIG. 17, the concentration of anti-biotin in the spiked sample was estimated to be 49.2±5.2 nM (n=3), yielding a percent recovery of 93.9%. Such a result indicates that the self-referencing localized plasmon resonance sensing system provides excellent compensation for color interference in the sample matrix.

Besides, anti-biotin in complex medium can be directly detected. For more details, many kinds of real samples, such as whole blood and plant saps, have very complex matrixes that will bias the results of direct biosensing in terms of RI difference between sample and blank, color interference, and nonspecific adsorption. However, in the present invention, a mimic complex sample composing of a high RI buffer and erythrosine as a color interfering substance is used to demonstrate the feasibility of the self-referencing localized plasmon resonance sensing system for direct detection of anti-biotin in such a complex sample. As shown in parts (C) and (D) of FIG. 16, which show a 1×PBS solution was injected into a sensor chip to establish flat baselines, and then various samples of erythrosine ($4\times10^{-5}$ g/mL) dissolved in 10×PBS buffer and spiked with increasing concentration of anti-biotin from 26.2 nM to 349 nM being sequentially injected into the sensor chip, and the compensated sensor response of the sixth embodiment of the present invention, respectively. From the calibration graph of $\Delta I_{S,SA}/I_{S0}$ versus log anti-biotin concentration as shown in FIG. 17, the plot has a linear relationship (correlation coefficient, r=0.9993, n=3) over the concentration range between 52.4 nM to 349 nM. The LOD of the self-referencing localized plasmon resonance sensing system for anti-biotin in such a complex medium was 31.8 nM, which is similar to that in 1×PBS (LOD=29.5 nM). To compare the results from samples in simple buffer and in complex matrix, statistical analysis of the results from these two groups was performed by pair-t test. Results show that the mean from each group agrees with each other at the 95% confidence interval, suggesting that the self-referencing localized plasmon resonance sensing system provides an easy, rapid, and high sensitivity method to detect analyte in complex samples.

Hence, a new approach to plasmon resonance biosensing based on a self-referencing dual-channel localized plasmon resonance sensing system is demonstrated in the present invention. This approach allows the use of a reference optical waveguide element for accurate compensation of systematic errors, such as temperature fluctuation, bulk refractive index change, color interference, and/or nonspecific adsorption, of the sensing optical waveguide element in a single microfluidic chip. The self-referencing mechanism would allow real-time localized plasmon resonance biosensing applications outside the laboratory where room temperature conditions cannot be held constant. It is also particularly useful for biosensing in complex real samples, in which interfering effects pose a great challenge for many label-free refractive-index-based biosensors. Since the localized plasmon resonance sensor is based on normalized response for data analysis, the need for precise optical alignment is alleviated. Hence, together with self-referencing mechanism for compensation of thermal and bulk-composition effects as well as nonspecific adsorption, the dual-channel localized plasmon resonance sensing system has potential advantages to be developed as a portable biosensor for on-site chemical and biochemical analysis in the fields of environment, agriculture, food, and healthcare.

The descriptions set forth hereinbefore are simply exemplary rather than being restrictive. All effectively equivalent modifications, changes or alternations made thereto without departing from the spirit and scope of the present invention are deemed as being encompassed by the field of the present invention defined as the following claims.

What is claimed is:

1. A self-referencing localized plasmon resonance sensing device, comprising:
    a reference optical waveguide element, modified with a first noble metal nanoparticle layer, and part of an incident light being guided into the reference optical waveguide element to generate a first localized plasmon resonance sensor signal;
    a sensing optical waveguide element being independent of the reference optical waveguide and modified with a second noble metal nanoparticle layer, the second noble metal nanoparticle layer being further modified with a recognition unit, and the other part of the incident light being guided into the sensing optical waveguide element to generate a second localized plasmon resonance sensor signal;
    a V-shaped channel with two legs connecting to the reference optical waveguide element and the sensing optical waveguide element respectively, and with a joint of the two legs being disposed with an opening for injecting a sample into the V-shaped channel such that the sample is guided into the reference optical waveguide element and the sensing optical waveguide element via the two legs; and
    a carrier placing the reference optical waveguide element and the sensing optical waveguide element.

2. The self-referencing localized plasmon resonance sensing device according to claim 1, wherein the first noble metal nanoparticle layer is modified at a reflecting surface of the reference optical waveguide element.

3. The self-referencing localized plasmon resonance sensing device according to claim 1, wherein the second noble metal nanoparticle layer is modified at a reflecting surface of the sensing optical waveguide element.

4. The self-referencing localized plasmon resonance sensing device according to claim 1, wherein the reference optical waveguide element and the sensing optical waveguide element are optical fibers, channel waveguides, planar waveguides, or tubular waveguides.

5. The self-referencing localized plasmon resonance sensing device according to claim 4, wherein when the reference optical waveguide element is the optical fiber, the first noble metal nanoparticle layer is modified at a stripped area or an end face of the optical fiber.

6. The self-referencing localized plasmon resonance sensing device according to claim 4, wherein when the sensing optical waveguide element is the optical fiber, the second noble metal nanoparticle layer is modified at a stripped area or an end face of the optical fiber.

7. The self-referencing localized plasmon resonance sensing device according to claim 1, wherein the self-referencing localized plasmon resonance sensing device is a microfluidic chip or an in-situ sampling and analysis device.

8. The self-referencing localized plasmon resonance sensing device according to claim 7, wherein the reference optical waveguide element and the sensing optical waveguide element are respectively constructed with a mirror at one end face of the reference optical waveguide element and at one end face of the sensing optical waveguide element, wherein the reference optical waveguide element and the sensing optical waveguide element are optical fibers or tubular waveguides.

9. The self-referencing localized plasmon resonance sensing device according to claim 8, wherein the reference optical waveguide element and the sensing optical waveguide element are further disposed with a filter membrane and a rigid holder with at least one opening, the mirrors are provided for reflecting the first localized plasmon resonance sensor signal and the second localized plasmon resonance sensor signal, the filter membrane sieves out interfering substances with sizes larger than that of an average pore size of the filter membrane, and the rigid holder encases the reference optical waveguide element and the sensing optical waveguide element in order to enhance the mechanical strength of the self-referencing localized plasmon resonance sensing device during a sampling operation.

10. The self-referencing localized plasmon resonance sensing device according to claim 1, wherein the recognition unit comprises a chemical recognition molecule, an antibody, an antigen, a lectin, a hormone receptor, a nucleic acid or a carbohydrate.

11. The self-referencing localized plasmon resonance sensing device according to claim 1,
    wherein the first localized plasmon resonance sensor signal includes a first signal generated by detecting a blank with the reference optical waveguide element and a second signal generated by detecting the sample with the reference optical waveguide element, wherein the reference optical waveguide element has a first calibration slope; the second localized plasmon resonance sensor signal includes a third signal generated by detecting the blank with the sensing optical waveguide element and a fourth signal generated by detecting the sample with the sensing optical waveguide element, wherein the sensing optical waveguide element has a second calibration slope;

wherein a processor normalizes a first difference between the second signal and the first signal and normalizes a second difference between the fourth signal and the third signal, wherein the processor utilizes the first calibration slope and the second calibration slope to regulate the second difference, which is normalized, for obtaining a regulated second difference, and then the processor utilizes a difference between the first difference, which is normalized, and the regulated second difference to obtain a sensor response;

wherein the sensor response are expressed by the following equation:

$$\frac{\Delta I_{S,SA}}{I_{S0}} = \frac{\Delta I_S}{I_{S0}} - \frac{\Delta I_{S,M}/I_{S0}}{\Delta I_{R,M}/I_{R0}} \times \frac{\Delta I_R}{I_{R0}};$$

wherein $\Delta I_{S,SA}$ represents the sensor response due to specific adsorption only, $I_{S0}$ represents the third signal generated by detecting the blank with the sensing optical waveguide element, $\Delta I_S$ represents the second difference between the fourth signal and the third signal, $\Delta I_{S,M}/I_{S0}$ and $\Delta I_{R,M}/I_{R0}$ respectively represent a normalized response of the sensing optical waveguide element and the reference optical waveguide element, which respectively indicate the second calibration slope and the first calibration slope, $\Delta I_R$ represents the first difference between the second signal and the first signal, and $I_{R0}$ represents the first signal generated by detecting the blank with the reference optical waveguide element.

12. A self-referencing localized plasmon resonance sensing system, comprising:
a light source generating an incident light;
a localized plasmon resonance sensing device, comprising:
a reference optical waveguide element, modified with a first noble metal nanoparticle layer, and part of the incident light being guided into the reference optical waveguide element to generate a first localized plasmon resonance sensor signal;
a sensing optical waveguide element being independent of the reference optical waveguide and modified with a second noble metal nanoparticle layer, the second noble metal nanoparticle layer being further modified with a recognition unit, and the other part of the incident light being guided into the sensing optical waveguide element to generate a second localized plasmon resonance sensor signal;
a V-shaped channel with two legs connecting to the reference optical waveguide element and the sensing optical waveguide element respectively, and with a joint of the two legs being disposed with an opening for injecting a sample into the V-shaped channel such that the sample is guided into the reference optical waveguide element and the sensing optical waveguide element via the two legs; and
a carrier placing the reference optical waveguide element and the sensing optical waveguide element;
at least one photodetecting unit receiving the first localized plasmon resonance sensor signal and the second localized plasmon resonance sensor signal, wherein the first localized plasmon resonance sensor signal includes a first signal generated by detecting a blank with the reference optical waveguide element and a second signal generated by detecting the sample with the reference optical waveguide element having a first calibration slope, the second localized plasmon resonance sensor signal includes a third signal generated by detecting the blank with the sensing optical waveguide element and a fourth signal generated by detecting the sample with the sensing optical waveguide element having a second calibration slope; and
a processor, normalizing a first difference between the second signal and the first signal and normalizing a second difference between the fourth signal and the third signal, wherein the processor utilizes the first calibration slope and the second calibration slope to regulate the second difference, which is normalized, for obtaining a regulated second difference, and then the processor utilizes a difference between the first difference, which is normalized, and the regulated second difference to obtain a sensor response.

13. The self-referencing localized plasmon resonance sensing system according to claim 12, wherein the first noble metal nanoparticle layer is modified at a reflecting surface of the reference optical waveguide element.

14. The self-referencing localized plasmon resonance sensing system according to claim 12, wherein the second noble metal nanoparticle layer is modified at a reflecting surface of the sensing optical waveguide element.

15. The self-referencing localized plasmon resonance sensing system according to claim 12, wherein the reference optical waveguide element and the sensing optical waveguide element are optical fibers, channel waveguides, planar waveguides, or tubular waveguides.

16. The self-referencing localized plasmon resonance sensing system according to claim 15, wherein when the reference optical waveguide element is the optical fiber, the first noble metal nanoparticle layer is modified at a stripped area or an end face of the optical fiber.

17. The self-referencing localized plasmon resonance sensing system according to claim 15, wherein when the sensing optical waveguide element is the optical fiber, the second noble metal nanoparticle layer is modified at a stripped area or an end face of the optical fiber.

18. The self-referencing localized plasmon resonance sensing system according to claim 12, wherein the localized plasmon resonance sensing device is a microfluidic chip or an in-situ sampling and analysis device.

19. The self-referencing localized plasmon resonance sensing system according to claim 18, wherein the reference optical waveguide element and the sensing optical waveguide element are respectively constructed with a mirror at one end face of the reference optical waveguide element and at one end face of the sensing optical waveguide element, wherein the reference optical waveguide element and the sensing optical waveguide element are optical fibers or tubular waveguides.

20. The self-referencing localized plasmon resonance sensing system according to claim 19, wherein the reference optical waveguide element and the sensing optical waveguide element are further disposed with a filter membrane and a rigid holder with at least one opening, the mirrors are provided for reflecting the first localized plasmon resonance sensor signal and the second localized plasmon resonance sensor signal, the filter membrane sieves out interfering substances with sizes larger than that of an average pore size of the filter membrane, and the rigid holder encases the reference optical waveguide element and the sensing optical waveguide element in order to enhance the mechanical strength of the localized plasmon resonance sensing device during a sampling operation.

21. The self-referencing localized plasmon resonance sensing system according to claim 12, wherein the recognition unit comprises a chemical recognition molecule, an antibody, an antigen, a lectin, a hormone receptor, a nucleic acid or a carbohydrate.

22. The self-referencing localized plasmon resonance sensing system according to claim 12, further comprising a lock-in amplifier enabling amplification of the first localized plasmon resonance sensor signal and the second localized plasmon resonance sensor signal as well as suppression of system noises.

23. The self-referencing localized plasmon resonance sensing system according to claim 12, wherein the sensor response are expressed by the following equation:

$$\frac{\Delta I_{S,SA}}{I_{S0}} = \frac{\Delta I_S}{I_{S0}} - \frac{\Delta I_{S,M}/I_{S0}}{\Delta I_{R,M}/I_{R0}} \times \frac{\Delta I_R}{I_{R0}};$$

wherein $\Delta I_{S,SA}$ represents the sensor response due to specific adsorption only, $I_{S0}$ represents the third signal generated by detecting the blank with the sensing optical waveguide element, $\Delta I_S$ represents the second difference between the fourth signal and the third signal, $\Delta I_{S,M}/I_{S0}$ and $\Delta I_{R,M}/I_{R0}$ respectively represent a normalized response of the sensing optical waveguide element and the reference optical waveguide element, which respectively indicate the second calibration slope and the first calibration slope, $\Delta I_R$ represents the first difference between the second signal and the first signal, and $I_{R0}$ represents the first signal generated by detecting the blank with the reference optical waveguide element.

* * * * *